United States Patent [19]

Sebastian

[11] Patent Number: 5,084,082
[45] Date of Patent: Jan. 28, 1992

[54] SOYBEAN PLANTS WITH DOMINANT SELECTABLE TRAIT FOR HERBICIDE RESISTANCE

[75] Inventor: Scott A. Sebastian, Hockessin, Del.

[73] Assignee: E. I. Du Pont de Nemours and Company, Wilmington, Del.

[21] Appl. No.: 481,543

[22] Filed: Feb. 20, 1990

Related U.S. Application Data

[63] Continuation-in-part of Ser. No. 247,963, Sep. 22, 1988, abandoned.

[51] Int. Cl.$^5$ .................. A01N 43/02; A01N 43/48; A01N 43/64; A01H 5/00
[52] U.S. Cl. .................. 71/90; 800/200; 800/230; 800/DIG. 26; 47/58; 435/172.1; 71/91; 71/92; 71/93
[58] Field of Search ............ 71/93, 94, 90, 91, 92; 47/58; 435/240.4, 172.1; 800/230, DIG. 26

[56] References Cited

U.S. PATENT DOCUMENTS

| | | | |
|---|---|---|---|
| 4,127,405 | 11/1978 | Levitt | 71/93 |
| 4,517,763 | 5/1985 | Beversdorf et al. | 47/53 |
| 4,545,146 | 10/1985 | Davis | 47/58 |
| 4,648,204 | 3/1987 | Davis | 47/58 |
| 4,699,649 | 10/1987 | Rorer | 71/90 |
| 4,761,373 | 8/1988 | Anderson | 435/172 |

OTHER PUBLICATIONS

Haughn et al. (1986) Mol. Gen. Genet. 204: 430-434.
Chaleff et al (1987) Mol. Gen. Genet. 210: 33-38.
Lee et al (May 1988) EMBOJ. 7: 1241-1248.
Mazur et al. (1987) Plant Physiology 85: 1110-1117.
Kishore et al (1988) Ann Re. Biochem. 57: 647-652.
Pinthus et al., *Science*, 177: 715-716 (1972).
Chamberlain et al., *Crop Science*, 8: 728-729 (1968).
*Agrichemical Age*, Jun. 1984 p. 20.
Estelle, *Trends in Genetics*, 2: 89-93 (1986).
Somerville, *Mol. Gen. Genetics*, 204: 430-434 (1986).
Hardcastle, *Weed Science*, 27: 278-279 (1979).
Feenstra et al., *Theor. Appl. Genet.*, 58: 39-42 (1980).
Sebastian et al., *Crop Science* 27: 948-952 (1987).
Chaleff et al., *Science* 223: 1148-1151 (1984).
Haughn et al., *Molecular and General Genetics* 211: 266-271 (1988).
Last et al., *Science* 240: 305-310 (1988).

*Primary Examiner*—Elizabeth C. Weimar
*Assistant Examiner*—Che Chereskin

[57] ABSTRACT

The utilization of a positive selection seed screening process to isolate rare variants with resistance to a herbicide is described. The ability to screen large numbers of mutagenized seed has made it feasible to pursue and isolate plants with low frequency dominant herbicide-resistance mutations. The dominant herbicide resistance mutations are useful for many applications including expanding the utility of sulfonylurea herbicides for soybean weed control, production of $F_1$ and $F_2$ seeds, and as selectable markers for efficient seed purification.

26 Claims, No Drawings

SOYBEAN PLANTS WITH DOMINANT SELECTABLE TRAIT FOR HERBICIDE RESISTANCE

CROSS-REFERENCE TO RELATED APPLICATION

This application is a continuation-in-part of copending application bearing U.S. Ser. No. 07/247,963, filed on Sept. 22, 1988, now abandoned.

FIELD OF THE INVENTION

This invention relates to selection of variants including low frequency dominant mutations conferring resistance to both pre- and post-emergent applications of certain herbicidal acetolactate synthase inhibitors.

BACKGROUND OF THE INVENTION

Mutation breeding techniques can be applied to develop new germplasm having desirable agronomic characteristics. Mutation breeding is initiated by generating a Population of plants with increased genetic variability through mutagenesis. The resulting population is then subjected to selective conditions which identify individuals expressing a desired trait or characteristic. Gottshalk et al., *Induced Mutations in Plant Breeding*, (Springer-Verlag, New York, 1983, PP. 16-17), and Simmonds, *Principles of Crop Improvement*, (Longman, N.Y., 1979, pp 297-303) are general references covering various mutation breeding techniques.

Mutations created using such procedures can occur at widely different frequencies, with highly desired traits often induced at extremely low rates. Where mutation frequencies are reasonably high, screening of the population to identify new traits has been accomplished by (1) exposure of progeny of the mutagenized population to a chemical treatment which kills unmodified specimens, or (2) inspection of plants germinated from the mutagenized seed for evidence of the new property. For example, Pinthus et al., Science. 177:715 (1972) described mutation breeding experiments involving herbicides. In these experiments, $M_2$ seed Populations of tomato and wheat were generated by soaking wheat and tomato seeds in 8 mM ethyl methanesulfonate (EMS). The treated seeds were then screened by sowing in soil containing the herbicides diphenamid or terbutryn at concentrations inhibitory to growth of the normal parental variety. The tolerant tomato lines obtained showed a 25% reduction in seedling weight in response to treatment with diphenamid, while the original cultivar exhibited a 40% reduction in seedling weight. Increased tolerance to herbicide was also reported for certain mutant wheat lines, although quantitative results were not provided.

Raut et al., *Indian J. Genet. Plant Breed*, 42:265-270 (1982), utilized chemical mutagenesis to induce and select mutations for a different seed coat color. Chamberlain and Bernard, *Crop Science*, 8:728-729 (1968) report the failure to obtain resistance to brown stem rot through mutagenesis despite the fact that such resistance can be found in nature.

*Agrichemical Age*, June 1984, p. 20, reports that USDA scientists W. L. Barrentine and E. E. Hartwig discovered variation with respect to tolerance for the herbicide metribuzin within the soybean cultivar *Glycine max* vc. "Tracy". Tolerant individuals were present at approximately a 5% frequency in the "Tracy" population, and were not mutants resulting from mutation breeding techniques.

There have been no reports of mutant soybean plants with altered acetolactate synthase (ALS) function associated with herbicide resistance.

Where mutations are extremely rare, many more seeds must be mutagenized and screened to obtain the new trait. It is well known that dominant mutations occur much less frequently than recessive mutations. In fact, to date, no one has ever selected a dominant mutation in soybean. Gottschalk et al., in their extensive review of mutation breeding, state that "about 1% of all induced mutations are dominant ones". This means that approximately 100 times as many individuals must be screened to find a dominant mutation as to find a recessive mutation. Using *Arabidopsis thaliana* as a model system, (Somerville, Trends in Genetics. 2: 89-93 (1986)) states that "for many loci, a mutation resulting in loss of function" (which is generally synonymous with a recessive mutation) "can be recovered by screening approximately 2000 M2 plants". Using these sources as guidelines, isolation of a dominant mutation in Arabidopsis could conceivably require screening of at least 200,000 M2 individuals depending on the locus in question and the vagaries of sampling the M2 population. The search for a dominant mutation, therefore, requires 100 times the work of a search for a recessive mutation. Such experiment size or labor is totally impractical. Due to the minute seed size of *Arabidopsis thaliana*, Somerville (Mol. Gen. Genet. (1986) 204: 430-434) was, however, able to isolate dominant chlorsulfuron-resistant mutants by screening up to 10,000 M2 seeds on a single 90 mm petri plate. Hardcastle [Hardcastle W. S. 1979. Soybean (*Glycine max*) cultivar response to metribuzin in solution culture. *Weed Science* (27):278-279] discloses the use of hydroponics to study the response of small numbers of soybean cultivars to a single concentration of metribuzin. Feenstra and Jacobsen, (TAG 58:39-42) disclose the use of hydroponics to select a recessive pea mutant lacking nitrate reductase (NR) activity. Their selection system consisted of growing seedlings for 7 days in moist vermiculite, removing the cotyledons, and trans- planting the seedlings to a small pan (22.5×22.5×5.5 cm) containing vermiculite and a nutrient solution. Five days later (when the plants were 12 days old), the nutrient solution was eventually supplemented with a chlorate solution. Since NR reduces chlorate to chlorite, which is toxic to plants, plants lacking NR could be selected based on their lack of chlorate damage. Since the plants were not treated with chlorate until they were seedlings of considerable age (12 days) and size, plant spacing to permit normal growth and visual observation must have limited the density (Plants Per unit area) at which seedlings were screened. Feenstra and Jacobsen screened 12 M2 seedlings from each of 1090 fertile plants. Although this procedure enabled them to screen enough M2 plants (roughly 13,080) to find one recessive NR mutant, transplanting and plant spacing would make it extremely laborious and space consuming to screen the population size required to find a dominant mutation.

One highly desirable agronomic characteristic currently sought in elite, commercial germplasm of a number of crop plants is true herbicide resistance. If selected within an elite soybean cultivar, a dominant soybean mutation conferring herbicide resistance could be immediately incorporated into an agronomic breeding program. Such mutations would be expected to be extremely rare, however, and no dominant mutation of any type has been discovered through seed mutagenesis and reported for soybean. Specifically, a dominant mutation that decreased the sensitivity of the target enzyme acetolactate synthase (ALS) to compounds that are herbicidal due to the inhibition of ALS was desired. Such resistance would require a specific change that renders the ALS enzyme resistant to the herbicide to insure that a cultivar would sustain little or no injury when exposed to the herbicidal compound, either in screening operations or in the field for weed control. It has been found that seed mutagenesis and mutant selection from a population of up to one million seeds is required to isolate a dominant, herbicide resistant plant mutation. A clear need exists for such dominant mutant plants as a basis to develop commercial soybean cultivars efficiently without sacrificing existing agronomic traits.

SUMMARY OF THE INVENTION

Applicant has utilized mutation breeding and hydroponic positive selection screening methods to discover soybean plants containing at least one dominant mutation capable of being expressed in subsequent generations of said plant and conferring resistance to pre- and post-emergent application of ALS-inhibiting herbicides, such as sulfonylaureas, triazolopyrimidine sulfonamides, imidazolinones or heteroaryl ethers.

Preferred are soybean plants, selected by mutation breeding, resistant to herbicidal sulfonylureas of Formula I:

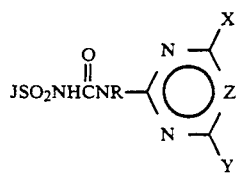

wherein
R is H or CH₃;
J is

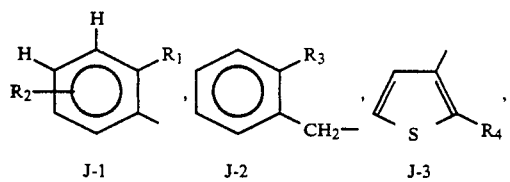

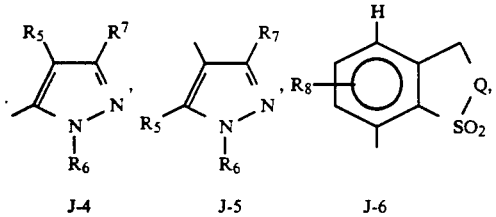

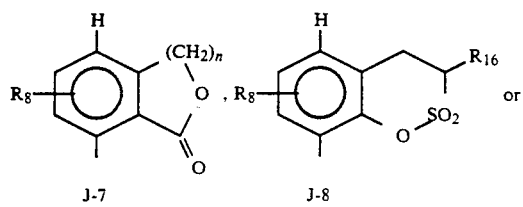

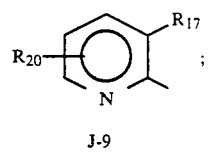

$R_1$ is Cl, Br, NO₂, $C_1$-$C_4$ alkyl, $C_2$-$C_4$ alkenyl, CF₃, $C_1$-$C_4$ alkoxy, $C_1$-$C_4$ haloalkoxy, $C_3$-$C_4$ alkenyloxy, $C_2$-$C_4$ haloalkenyloxy, $C_3$-$C_4$ alkynyloxy, CO₂R₉, CONR₁₀R₁₁, S(O)mR₁₂, OSO₂R₁₂, phenyl, SO₂N(OCH₃)CH₃, SO₂NR₁₀R₁₁,

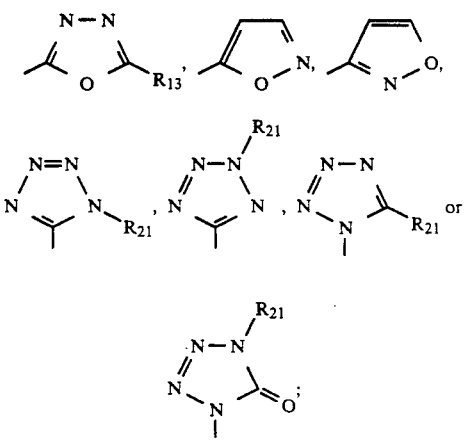

$R_2$ is H, Cl, Br, F, CH₃, NO₂, SCH₃, OCF₂H, OCH₂CF₃ or OCH₃;
$R_3$ is Cl, NO₂, CO₂CH₃, CO₂C₂H₅, SO₂N(CH₃)₂, SO₂CH₃ or SO₂C₂H₅;
$R_4$ is $C_1$-$C_3$ alkyl, Cl, Br, NO₂, CO₂R₉, CON(CH₃)₂, SO₂N(CH₃)₂, SO₂N(OCH₃)CH₃ or S(O)$_m$R₁₂;
$R_5$ is $C_1$-$C_3$ alkyl, $C_4$-$C_5$ cycloalkylcarbonyl, F, Cl, Br, NO₂, CO₂R₁₄, SO₂N(CH₃)₂, SO₂R₁₂ or phenyl;
$R_6$ is H, $C_1$-$C_3$ alkyl or CH₂CH=CH₂;
$R_7$ is H, CH₃, OCH₃, Cl or Br;
$R_8$ is H, F, Cl, Br, CH₃, OCH₃, CF₃, SCH₃ or OCF₂H;
$R_9$ is $C_1$-$C_4$ alkyl, $C_3$-$C_4$ alkenyl or CH₂-CH₂Cl;
$R_{10}$ is H or $C_1$-$C_3$ alkyl;
$R_{11}$ is H or $C_1$-$C_2$ alkyl;
$R_{12}$ is $C_1$-$C_3$ alkyl;
$R_{13}$ is H or CH₃;
$R_{14}$ is $C_1$-$C_3$ alkyl or CH₂CH=CH₂;
m is 0, 1 or 2;
n is 1 or 2;
Q is CH₂, CHCH₃ or NR₁₅;
$R_{15}$ is H or $C_1$-$C_4$ alkyl;
P is O or CH₂;
$R_{16}$ is H or CH₃;
$R_{17}$ is C(O)NR₁₈R₁₉, CF₃, COOCH₃ or SO₂CH₂CH₃;
$R_{18}$ is H or CH₃;
$R_{19}$ is CH₃;
$R_{20}$ is H, Cl, F, Br, CH₃, CF₃, OCH₃ or OCF₂H;
$R_{21}$ is H or CH₃;
X is CH₃, OCH₃, OC₂H₅ or NHCH₃;
Y is CH₃, C₂H₅, OCH₃, OC₂H₅, OCF₂H, OCH₂CF₃, Cl, CH₂OCH₃ or cyclopropyl;
Z is CH or N;

and their agriculturally suitable salts; provided that
a) when Y is Cl, then Z is CH and X is OCH₃;
b) when Y is OCF₂H, then Z is CH;
c) when J is J-1 and R₁ is OSO₂R₁₂ or phenyl, then Y is other than OCF₂H;
d) when J is J-2, then Y is other than OCF₂H or OCH₂CF₃; and
e) when J is J-3 and R₄ is S(O)ₘR₁₂, then Y is other than OCH₂CF₃.

Sulfonylurea herbicides to which the soybean lines or cultivars are particularly resistant include:
1) Compounds of Formula I where
   J is J-1;
   R₁ is Cl, CH₃, C₁-C₄ alkoxy, C₁-C₂ haloalkoxy allyloxy, propargyloxy, CO₂R₉, CONR₁₀R₁₁, SO₂N-(OCH₃)CH₃, SO₂NR₁₀R₁₁, S(O)ₘR₁₂, OSO₂R₁₂, phenyl or

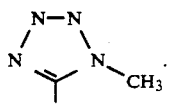

2) Compounds of Formula I where
   J is J-2;
   R is H; and
   R₃ is SO₂N(CH₃)₂, CO₂CH₃ or CO₂C₂H₅
3) Compounds of Formula I where
   J is J-3
   R is H; and
   R₄ is CO₂CH₃ or CO₂C₂H₅;
4) Compounds of Formula I where
   J is J-4;
   R is H;
   R₅ is Cl, Br, CO₂CH₃, CO₂C₂H₅ or

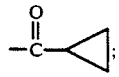

R₆ is CH₃; and
   R₇ is H, Cl or OCH₃.
5) Compounds of Formula I where
   J is J-5;
   R is H;
   R₅ is CO₂CH₃ or CO₂C₂H₅; and
   R₇ is H or CH₃.
6) Compounds of Formula I where
   J is J-6;
   Q is CHCH₃ or NR₁₅;
   R is H; and
   R₈ is H, F, Cl, CH₃, OCH₃, CF₃ or SCH₃.
7) Compounds of Formula I where
   J is J-7;
   R is H; and
   R₈ is H, F, Cl, CH₃, OCH₃, CF₃ or SCH₃.
8) Compounds of Formula I where
   J is J-8;
   R is H:
   R₁₆ is CH₃; and
   R₈ is H, F, Cl, CH₃, OCH₃, CF₃ or SCH₃.
9) Compounds of Formula I where
   J is J-9;
   R is H; and
   R₁₇ is C(O)N(CH₃)₂, CF₃, COOCH₃ or SO₂CH₂CH₃.
10) Compounds of Formula I where
    R is H;
    R₁ is Cl, C₁-C₄ alkoxy, OCF₂H, OCH₂CH₂Cl, CO₂R₉, CON(CH₃)₂, SO₂N(CH₃)₂, SO₂R₁₂ or OSO₂R₁₂; and
    R₂ is H, Cl, CH₃, or OCH₃.

Sulfonylurea herbicides to which the soybean lines or cultivars are more particularly resistant include:
2-chloro-N-[(4-methoxy-6-methyl-1,3,5-triazin-2-yl) aminocarbonyl]benzenesulfonamide,
methyl 2-[[[[(4,6-dimethyl-2-pyrimidinyl)-amino]carbonyl]amino]sulfonyl]benzoate,
methyl 2-[[[[(4-methoxy-6-methyl-1,3,5-triazin-2-yl)amino]carbonyl]sulfonyl]-benzoate,
2-[[N-(4-methoxy-6-methyl-1,3,5-triazin-2-yl)-N-methylaminocarbonyl]aminosulfonyl]-benzoic acid, methyl ester,
ethyl 2-[[[[(4-chloro-6-methoxy-2-pyrimidinyl)amino]-carbonyl]amino]sulfonyl]benzoate,
2-[[(4-ethoxy-6-methylamino-1,3,5-triazin-2-yl)aminocarbonyl]aminosulfonyl]benzoic acid, methyl ester,
2-[[(4,6-dimethoxy-1,3,5-triazin-2-yl)aminocarbonyl]aminosulfonyl]-4-(2,2,2-trifluoroethoxy)benzoic acid, ethyl ester,
4-chloro-2-[[(4-methoxy-6-methyl-1,3,5-triazin-2-yl)aminocarbonyl]aminosulfonyl]-benzoic acid, isopropyl ester,
3-[[[[(4-methoxy-6-methyl-1,3,5-triazin-2-yl)-amino]carbonyl]amino]sulfonyl]-2-thiophene carboxylic acid, methyl ester,
methyl 2-[[[[(4-6-dimethoxy-2-pyrimidinyl)-amino]carbonyl]amino]sulfonyl]methylbenzoate,
2-[[(4,6-dimethoxypyrimidin-2-yl)aminocarbonyl]aminosulfonyl]-N,N-dimethyl-3-pyridinecarboxamide,
2-[[(4,6-dimethoxypyrimidin-2-yl)aminocarbonyl]aminosulfonyl]-3-pyridinecarboxylic acid, methyl ester,
N-[(4,6-dimethoxypyrimidin-2-yl)aminocarbonyl]-3-(ethylsulfonyl)-2-pyridinesulfonamide,
N-[4,6-dimethoxypyrimidin-2-yl)aminocarbonyl]-2,3-dihydro-2-methyl-benzo(b)thiophene-7-sulfonamide, 1,1 dioxide,
2[[[[(4,6-bis(difluoromethoxy)-2-pyrimidinyl]-amino]-carbonyl]amino]sulfonyl]benzoic acid, methyl ester,
ethyl 5-[3-(4,6-dimethoxypyrimidin-2-yl)ureidosulfonyl]-1-methylpyrazole-4-carboxylate,
N-[(6-methoxy-4-methyl-1,3,5-triazin-2-yl)aminocarbonyl]-2-(2-chloroethoxy)benzene sulfonamide, and
N-[(4,6-dimethoxy-1,3,5-triazin-2-yl)aminocarbonyl]-3-trifluoromethyl-2-pyridinesulfonamide.

Most preferred are those soybean plants bearing a dominant mutation conferring resistance to methyl2-[[[[(4,6-dimethyl-2-pyrimidinyl)-amino]carbonyl]sulfonyl]benzoate.

Also preferred are soybean lines or cultivars, isolated by mutation breeding, resistant to herbicidal triazolopyrimidine sulfonamides of Formula II:

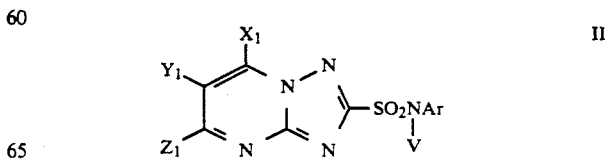

wherein
Ar is

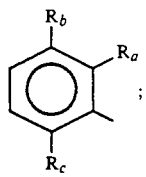

$R_a$ is $C_1$-$C_4$ alkyl, F, Cl, Br, I, NO$_2$, S(O)$_p$R$_d$, COOR$_e$ or CF$_3$;

$R_b$ is H, F, Cl, Br, I, $C_1$-$C_4$ alkyl, CF$_2$ or COOR$_e$;

$R_c$ is H, $C_1$-$C_4$ alkyl, F, Cl, Br, I, CH$_2$OR$_d$, CF$_2$, phenyl, NO$_2$ or COOR$_e$;

$R_d$ is $C_1$-$C_4$ alkyl;

$R_e$ is $C_1$-$C_4$ alkenyl, $C_1$-$C_4$ alkynyl, or 2-ethoxyethyl;

V is H, $C_1$-$C_3$ alkyl, allyl, propargyl, benzyl or $C_1$-$C_3$ alkylcarbonyl;

$X_1$, $Y_1$, and $Z_1$, are independently H, F, Cl, Br, I, $C_1$-$C_4$ alkyl $C_1$-$C_2$ alkylthio or $C_1$-$C_4$ alkoxy; and p is 0, 1 or 2.

Triazolopyrimidine sulfonamide herbicides include:
1) Compounds of Formula II
2) Compounds of Preferred 1 where
   $X_1$ is H or CH$_3$;
   $Y_1$ is H;
   $Z_1$ is CH$_3$; and $R_a$ and $R_c$ are not simultaneously H.

These triazolopyrimidine sulfonamide compounds are known inhibitors of ALS and are very similar to sulfonylureas in structure/activity relationships.

Also preferred are soybean lines or cultivars, isolated by mutation breeding, resistant to herbicidal imidazolones of Formula III:

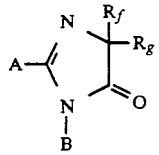

wherein
A is

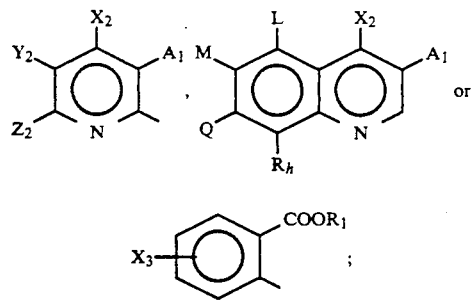

$R_f$ is $C_1$-$C_4$ alkyl;
$R_g$ is $C_1$-$C_4$ alkyl or $C_3$-$C_6$ cycloalkyl;
$A_1$ is COOR$_i$, CH$_2$OH or CHO;
$R_i$ is H; $C_1$-$C_{12}$ alkyl optionally substituted by $C_1$-$C_3$ alkyl, $C_3$-$C_6$ cycloalkyl or phenyl; $C_3$-$C_5$ alkenyl optionally substituted by phenyl or 1-2 $C_1$-$C_3$ alkyl, F, C$_1$, Br or I; or $C_3$-$C_5$ alkynyl optionally substituted by phenyl or 1-2 $C_1$-$C_3$ alkyl, F, Cl, Br or I;
B is H; C(O)$C_1$-$C_6$ alkyl or C(O)phenyl optionally substituted by Cl, NO$_2$ or OCH$_3$;

$X_2$ is H, F, Cl, Br, I, OH or CH$_3$;

$Y_2$ and $Z_2$ are independently H, $C_1$-$C_6$ alkyl, $C_1$-$C_6$ alkoxy, F, Cl, Br, I, phenyl, NO$_2$, CN, CF$_3$ or SO$_2$CH$_3$; or $Y_2$ and $Z_2$ together with the carbon atoms to which they are attached form a 5- or 6-membered saturated or unsaturated ring containing 1-3 heteroatoms selected from the group consisting of 0-2 oxygen, 0-2 sulfur and 0-3 nitrogen atoms; said ring may be unsubstituted or substituted on carbon or nitrogen wherein the substituents are selected from the group consisting of $C_1$-$C_4$ alkyl, $C_1$-$C_4$ haloalkyl, $C_3$-$C_6$ alkenyl, $C_3$-$C_6$ haloalkenyl, $C_3$-$C_4$ alkynyl, $C_3$-$C_4$ haloalkynyl, $C_1$-$C_4$ alkoxy, $C_1$-$C_4$ haloalkoxy, $C_1$-$C_4$ alkoxycarbonyl, phenyl, $C_1$-$C_4$ dialkylamino and $C_1$-$C_4$ alkylsulfonyl;

L is M, Q and Rh are independently H, F, Cl, Br, I, CH$_3$, OCH$_3$, NO$_2$, CF$_3$, CN, N(CH$_3$)$_2$, NH$_2$, SCH$_3$ or SO$_2$CH$_3$ provided that only one of M or Q may be a substituent other than H, F, Cl, Br, I, CH$_3$ or OCH$_3$.

Preferred are the above wherein:
B is H; and
$A_1$ is COOR$_i$.

Most preferred are the above wherein:
$R_f$ is CH$_3$;
$R_g$ is CH(CH$_3$)$_2$;
$X_2$ is H;
$Y_2$ is H or $C_1$-$C_3$ alkyl or OCH$_3$;
$Z_2$ is H;
$X_3$ is H, CH$_3$, Cl or NO$_2$; and
L, M, Q and $R_h$ are H.

These herbicidal imidiazolinones are also known inhibitors of ALS.

This invention also relates to seed obtained by growing the soybean plants of the invention.

Another embodiment of this invention involves a method for controlling the growth of undesired vegetation growing at the locus where a soybean plant of the invention has been cultivated comprising applying to the locus an effective amount of a compound of Formula I-III. Preferred is the method wherein the compound applied is methyl 2-[[[[(4,6-dimethyl-2-pyrimidinyl)amino]carbonyl]amino]sulfonyl]benzoate.

DETAILED DESCRIPTION OF THE INVENTION

The present invention describes plants with rare dominant herbicide-resistance mutations obtained by a hydroponic seed selection process. The ideal method for screening and selecting the products of a mutation breeding program should be uniform, quick, nondestructive, labor saving, space efficient, and should approximate the actual field conditions that must be tolerated. These qualities are especially important when looking for a mutation that is extremely rare. Most methods of herbicide treatment lack one or more of the above qualities. For example, field treatments lack the uniformity of treatment necessary to prevent "escapes" or plants that were not fully exposed to the intended dose of herbicide. Escapes can result from shading of one plant by another during foliar application, emergence of late germinators after a foliar treatment, nonuniform soil incorporation of a preemergence-applied herbicide, uneven watering of herbicide-treated soil, or malfunctions in the spraying apparatus. Greenhouse pot treatments generally have better uniformity than field treatments but are labor intensive and space consuming.

A seed soak treatment for selection is possible, but does not closely approximate field treatment conditions since the plants are only exposed to the herbicide for several hours. Although some useful variants can be identified with a seed soak procedure, many false leads are also selected which require rechallenges with herbicide or genetic tests to weed out the escapes. For example, a genetic variation that prevents movement of a herbicide through the seed coat would not protect the plant once the seed coat is broken by the germinating seedling.

It is believed that an extremely efficient and effective positive selection screening method is provided by a hydroponic system resulting from the combination of five features.

1. an inert planting medium to permit quick direct planting of seeds, physical support, and adequate aeration and uniform germination of densely planted seeds;
2. a closed-loop irrigation system consisting of a water soluble toxin solution reservoir used to irrigate and receive drainage from a planting tank;
3. automated or manual irrigation to ensure periodic flooding of the planting medium with a known concentration of the water soluble toxin;
4. irrigation and soaking of a level planting tank to ensure uniform treatment of seedlings with a known toxin concentration; and
5. periodic drainage of solution from the planting medium to provide proper aeration for healthy growth.

The present hydroponic system invention can rapidly and uniformly screen at least 16,000 soybean seedlings per square meter of greenhouse bench space in less than 10 days. With this system, one can screen 1,000,000 soybean seedlings in about 60 days with 10 square meters of greenhouse bench space. For small seeded crops, much larger populations could be screened per unit greenhouse space. This system has permitted the successful isolation of the novel soy-bean mutant plants described herein.

In the context of this disclosure, a number of terms shall be utilized. As used herein, the term "variant" refers to any individual that differs from the general population in terms of expressing a specific trait. A variant can result from an induced or spontaneous mutation or from selection within any collection of germplasm. "Mutation" refers to a detectable and heritable genetic change not caused by segregation or genetic recombination. A "dominant mutation" refers to a genetic change that is expressed in the heterozygous condition. Such dominant mutations are "completely dominant" if expressed to the same degree as in the homozygous state, and are "semidominant" when partially expressed in the hetero- zygous condition. "Recessive mutation" refers to a genetic change that is only expressed when in the homozygous condition. A "low frequency mutation" refers to a genetic change that retains and/or improves a gene's biochemical capacity; usually inherited as a dominant or semidominant trait and usually much less frequent than a recessive mutation. In contrast, a "high frequency mutation" refers to a genetic change that causes the loss of a gene and/or the gene's resulting biochemical capacity; usually inherited as a recessive trait and much more frequent than a dominant mutation. The term "tolerance" means the heritable ability of a plant to sustain less damage than other individuals of a given species in the presence of an injurious concentration of a toxin or pathogen, while "resistance" refers to a heritable ability to survive (with agronomically acceptable injury) a concentration of toxin or pathogen that is normally lethal or severely injurious to individuals of given species.

As used herein, the term "mutant" refers to an individual or lineage of individuals possessing a genetic mutation. "Plants" are individuals of any species in the Plantae Kingdom, while "cultivar" means a line that is fully characterized, named, and intended for use by farmers. Cultivar is synonymous with "variety". The term "mutation breeding" refers to the use of a mutagenic agent to induce random genetic mutations within a population of individuals. The treated population or subsequent generations of that population are then screened for desirable mutations than can be used in a breeding program. A "population" is any group of individuals which share a common gene pool. In the instant case, this includes Ml, M2, M3, M4, Fl, F2, and F3 populations. As used herein, and "Ml population" is the seeds (and resulting plants) exposed to a mutagenic agent, while "M2 population" is the progeny of self-pollinated Ml plants, "M3 population" is the progeny of self-pollinated M2 plants, "M4 population" is the progeny of self-pollinated M3 plants, and generally "Mn population" is the progeny of self-pollinated Mn-1 plants. The term "mutagen-treated population" refers to any population resulting from a mutagenic treatment (including the Ml and subsequent generations), while a "line" is a group of individuals from a common ancestry. For example, a mutant line is the progeny of a selected ancestor which all possess the heritable mutant trait of that ancestor.

In that context of this disclosure the term "positive selection" refers to a selection procedure in which only the desired individuals survive (or develop normally) in the presence of a selective toxin, while "negative selection" means a procedure in which the desired individuals are selected as abnormal, delayed, or inhibited in growth in the presence of the selective toxin. The term "hydroponic" refers to culture of plants in water (in the absence of soil); in the present application, the plants are supported by an inert planting medium (e.g., vermiculite) that is irrigated with water (with or without added nutrients). The term "inert planting medium" refers to a medium that does not significantly alter or chemically react with the solution that the medium supports; used primarily for physical support of the seeds and resulting plants. As used herein, "irrigation" means flushing the hydroponic system with a solution channeled from a reservoir, while "subirrigated" refers to irrigation by increasing the water level from below and up through the suspended planting medium. The term "aeration" means to provide plant roots with a supply of air (containing oxygen) that permeates the planting medium after nonadsorbed irrigation water is drained from the planting medium. As used herein, "closely-packed or densely-planted seeds" refers to the planting of seeds as densely as possible (touching) in a single horizontal layer. Actual density per unit area depends on seed size.

Hydroponic Positive Selection Method

The hydroponic selection system can be used to efficiently screen any seed-propagated plant species for induced or natural genetic variation for tolerance/resistance to any water soluble toxin that exerts an observable effect on seeds or developing seedlings. Seed-propagated plant species suitable for use with the hydroponic method include any species in the Kingdom Plantae that produces seeds that are capable of germination, emergence, and further development when densely planted in an inert medium that is both aerated and moistened with water or an aqueous nutrient solution, including; corn, alfalfa, oats, millet, wheat, rice, barley, sorghum, soybean, petunia, cotton sugarbeets, sunflower, carrot, celery, flax, cabbage, cucumber, pepper, canola, tomato, potato, lentil, broccoli, tobacco, amaranth, bean, asparagus, lettuce, rape, and other crop plants.

Efficiency of the screen is limited only by the density at which seeds of a given species can be planted in a single horizontal layer and the time required for that species to develop to the point where the herbicide's effect can be observed. Efficiency of the screen can therefore be defined as the number of individuals that can be screened per unit area per unit time.

Induced genetic variation includes mutations resulting from any deliberately applied mutagenic agent including physical mutagens such as X-rays, gamma rays, fast or thermal neutrons, protons, and chemical mutagens such as ethyl methane sulfonate (EMS), diethyl sulfate (DES), ethylene imine (EI), propane sulfone, N-methyl-N-nitroso urethane (MNU), nitrosomethyl urea (NMU), ethylnitrosourea (ENU), and other chemical mutagens.

Natural variation includes germplasm collections, mixed seed lots, a collection of lines or segregating populations generated from a breeding program, or spontaneous mutations within any line or population.

Herbicide resistance represents an important trait in crop plants in light of current weed-control strategies. Representative examples of herbicides which are useful for mutant selection, either individually or in combination with any other herbicide, are those of the sulfonylurea, triazine, triazole, uracil, urea, amide, diphenyl ether, carbamate, imidazolinone, cineole and bipyridylium types.

In addition, a number of compounds found to inhibit acetolactate synthase (ALS) have proven useful as herbicides and would also be useful individually or in combination with other herbicides as water soluble toxins in the selection of mutants. Mutant plants of the present invention are resistant to ALS-inhibiting herbicides such as sulfonylureas, triazolopyrimidine sulfonamides, imidazolinones and heteroaryl ethers. These herbicides are disclosed in the following patents and published patent applications as follows:

| Sulfonylureas | |
| --- | --- |
| U.S. Pat. No. 4,127,405 | U.S. Pat. No. 4,383,113 |
| U.S. Pat. No. 4,169,719 | U.S. Pat. No. 4,394,153 |
| U.S. Pat. No. 4,190,432 | U.S. Pat. No. 4,394,506 |
| U.S. Pat. No. 4,214,890 | U.S. Pat. No. 4,420,325 |
| U.S. Pat. No. 4,225,337 | U.S. Pat. No. 4,452,628 |
| U.S. Pat. No. 4,231,784 | U.S. Pat. No. 4,481,029 |
| U.S. Pat. No. 4,257,802 | U.S. Pat. No. 4,586,950 |
| U.S. Pat. No. 4,310,346 | U.S. Pat. No. 4,435,206 |
| U.S. Pat. No. 4,544,401 | U.S. Pat. No. 4,514,212 |
| U.S. Pat. No. 4,435,206 | U.S. Pat. No. 4,634,465 |

Triazolopyrimidine sulfonamides
EP-A 150,974
South African Application 84/8844 (published 5/14/85)
Imidazolinones
U.S. Pat. No. 4,188,487
EP-A 41,623
Heteroaryl Ethers
EP-A 249,707
EP-A 249-708
Other ALS-inhibiting herbicides
U.S. Pat. No. 4,838,925 (heterocyclic aryl sulfonamides)
U.S. Pat. No. 4,761,173 (heterocyclic sulfonamides)

Table I lists a number of herbicidal compounds specifically utilized in developing applicant's soy-bean plant invention.

TABLE I

Herbicidal Compounds For Soybean Mutant Characterization

Compound 1: 2-chloro-N-[[(4-methoxy-6-methyl-1,3,5-triazin-2-yl)amino]carbonyl]benzenesulfonamide Compound 2: Methyl 3-[[[[(4-methoxy-6-methyl-1,3,5-triazine-2-yl)amino]carbonyl]amino]sulfonyl]-2-thiophenecarboxylate Compound 3: Methyl 2-[[[[N-(4-methoxy-6-methyl-1,3,5-triazin-2-yl)N-methylamino]carbonyl]amino]sulfonyl]benzoate Compound 4: Methyl 2-[[[[(4,6-dimethyl-2-pyrimidinyl)amino]carbonyl]amino]sulfonyl]benzoate Compound 5: Ethyl 2[[[[(4-chloro-6-methoxy-2-pyrimidinyl)amino]carbonyl]amino]sulfonyl]benzoate Compound 6: 2-[[[[(4,6-dimethoxy-2-pyrimidinyl)amino]carbonyl]amino]sulfonyl]N,N-dimethyl-3-pyridinecarboxamide Compound 7: N-[[(4,6-dimethoxy-2-pyrimidinyl)amino]carbonyl]-3-(ethylsulfonyl)-2-pyridinesulfonamide Compound 8: Methyl 2-[[[[(4,6-dimethoxy-2-pyrimidinyl)amino]carbonyl]amino]sulfonyl]-3-pyridinecarboxylate Compound 9: 2-[4,5-dihydro-4-methyl-4-(1-methylethyl)-5-oxo-1H-imidazol-2-Yl]-3-quinolinecarboxylic acid Compound 10: 5-ethyl-2-[4,5-dihydro-4-methyl-4-(1-methylethyl)-5-oxo-1H-imidaxol-2-yl]-3-quinolinecarboxylic acid Compound 11: 2-[4,5-dihydro-4-methyl-4-(1-methylethyl)-5-oxo-1H-imidazol-2-yl]-3-pyridinecarboxylic acid, 1-methylethanamine salt Compound 12: N-[[(4,6-dimethoxy-2-pyrimidinyl)amino]carbonyl]-2,3,-dihydro-2-methylbenzo [B] thiophene-7-sulfonamide, 1,1-dioxide The hydroponic nutrient solution can consist merely of distilled water or tap water if seed reserves of the species of interest are capable of supporting germination and development to the point where the selective herbicides effect can be observed. Additional soluble nutrients can be added to the nutrient solution in cases where such nutrients are needed to achieve germination, emergence, and development of the seedlings to the point where the selective herbicides effect can be observed. Pilot runs of the hydroponic system in the absence of the selective herbicides can be used to determine how far development can proceed in the absence or presence of water soluble nutrients. Once these conditions are established, a lethal concentration of the herbicides can be included as a component of the nutrient solution so that only resistant individuals will develop normally.

Small-Scale prototype for Hydroponic Screening System

A number of small-scale hydroponic systems are commercially available. These systems were designed to promote quick lush growth of transplanted seedlings and not intended for use as a screen of germinating seedlings. It became immediately apparent that the commercial systems, if operated as advertised, lacked two key features necessary for an efficient screen: direct seeding and dense planting. However, the commercially available systems provided a convenient framework for modification with these features. The applicant utilized two such systems called the Hydropot Solo and the Hydropot Quad from Applied Hydroponics (San Rafael, CA, 94901). Since both systems operate by the same principles, only one system, the Hydropot Solo will be described in detail.

The Hydropot Solo consists of a plastic reservoir (48 cm×38 cm×13 cm) which supplies nutrient solution to a plastic planting tank (48 cm×35 cm×18 cm) that is placed directly on top of the reservoir. A small electric pump is used to pump nutrient solution from the reservoir up through a hole in the bottom of the planting tank. Applied Hydroponics also supplies the Hydropot Solo system with an inert soil substitute called Geolite which is used to fill the planting tank. Geolite is a porous rock-like material (pebbles approximately 1 cm in diameter) that is adequate to hold the moisture supplied by the reservoir and provide physical support for established plants. Irrigation of the planting tank is controlled by a 24-hour programmable electric timer that turns the pump on and off at desired preset time intervals. When the pump is activated, nutrient solution is pumped through plastic tubing up through a hole in the bottom of the planting tank. The solution level continues to rise within the planting tank until it reaches a depth of 9 cm. At this depth a drain valve returns the excess nutrient solution to the reservoir. The water level will remain at the level of the drain valve until the pump is deactivated. The remainder of the nonadsorbed nutrient solution then drains from the planting tank into the reservoir through a small hole in the bottom of the planting tank. The Hydrofarm Quad system is identical to the Hydrofarm Solo in concept. However, in the Quad system, a larger reservoir is used to irrigate four planting tanks instead of just one. To develop an efficient system, the hydropot system had to be modified to allow direct planting of densely-planted seeds.

The intended use of the Hydropot systems is to transplant established seedlings into the Geolite medium and grow the seedlings to maturity—not to screen germinating seeds. The Geolite stones were not suitable to permit direct seeding of crop plants. The stones were too large (approx. 1 cm in diameter) to prevent the seeds from falling down in between the stones; this would have resulted in seeds planted at nonuniform depth. To permit direct seeding, the Geolite pebbles had to be replaced with a planting medium that was both inert and of fine enough texture to support seeds in a single level horizontal layer. This would promote uniform emergence and uniform toxin exposure. A pilot study showed that vermiculite (particle size approx. 2 mm) was an ideal planting medium since it was lightweight, inert, and promoted quick seedling emergence and growth in the absence of toxin. The chosen design for future experiments consisted of the planting tank filled first with 3 cm of pea gravel or geolite and then covered with 13 cm of vermiculite. Seeds were planted 2 cm deep into the vermiculite. The lower layer of pea gravel served to distribute the influx of irrigation solution horizontally first (because of the large pore size) and then vertically by capillary action as the solution level reached the finer vermiculite.

A pilot study was conducted to determine whether the modified Hydropot Solo system could be used to consistently differentiate between previously isolated (Sebastian and Chaleff, 1987. Crop Science 27:948-952) SU-tolerant mutants and wild type soybean plants. Four Hydropot Solo units were prepared with each planting tank containing a lower layer of pea gravel and an upper layer of fine vermiculite as described previously. Each reservoir was filled with tap water supplemented with ¼ tablespoon of Miracle Grow soluble fertilizer per gallon. One hydroponic unit served as an untreated control while the nutrient solution of each of the other three was supplemented with either 100, 300, or 1000 ppb of an experimental sulfonylurea herbicide Compound 12. Ten seeds each of Williams 82 (wild type soybean cultivar), mutant 1-184A, mutant 1-183A, mutant 1-166A, and mutant 1-126A were then planted 2 cm deep into the vermiculite layer of each of the four hydroponic units. The programmable timer was set to irrigate the planting tanks for four 30-minute intervals during each 24-hour period. At 10 days after planting, a consistent and clear difference between wild type and mutant soybean lines was observed in all three systems irrigated with Compound 12. At 100 ppb Compound 12, mutant plants were able to form both unifoliolate leaves and secondary roots while Williams 82 could not. Differences between mutant and wild type became less dramatic as the herbicide concentration increased to 1000 ppb. Prolonged exposure (20 to 28 days) to 100 ppb Compound 12 prevented further development of even the tolerant mutants. These observations confirmed that the modified Hydropot system could be used to select for herbicide tolerance. It also became apparent that the herbicide concentration and exposure time could be used to differentiate between different levels of herbicide tolerance/resistance.

Large-Scale Hydroponic Screening System

Using the modified Hydropot system as a prototype, two large hydroponic systems were constructed to screen soybean populations for resistance to sulfonylurea herbicides. Each system consists of a transparent plexiglass planting tank (1.77 m long×0.85 m wide×0.27 m deep) which rests on a level greenhouse bench. Each planting tank is irrigated with herbicide solution from a 200 l polyethylene reservoir that can be stored directly under or beside the greenhouse bench. Irrigation is initiated by a programmable timer that energizes a pump connecting the reservoir with the planting tank via plastic tubing. The pump is deenergized by an adjustable float level switch in the planting tank. The float level switch is adjusted so that it turns off the pump when the solution level reaches the desired level in the planting tank. Drain valves on the planting tank are also controlled by the programmable timer so that the irrigation solution (once filled to the level specified by the adjustable float) can be retained in the planting tank for any desired length of time. The desired soaking time is manually entered into the programmable timer at the beginning of each screening cycle. After the desired soaking time, drain valves on the planting tank are automatically opened and the irrigation solution is allowed to drain back into the reservoir by gravity.

The inside of each planting tank is divided with a horizontal (level) perforated metal platform to create an upper and lower chamber. The platform is supported with plexiglass beams that span the width and length of the lower chamber. These beams have regular gaps to allow free movement of solution within the lower chamber. The upper chamber is first covered with nylon mesh (to retain the planting medium) and then filled 7 cm deep with granular vermiculite which serves as the inert planting medium and support for developing plants. This layer of vermiculite is then leveled by dragging a thin straight board over the surface using the level top edge of the planting tank as a guide. The population of seeds to be screened is then scattered by hand over the level vermiculite. Seeding can be sparse or dense enough so that the seeds form a solid layer (about 12,000 to 13,000 seeds per square meter for soybean). Small-seeded soybean populations or other small-seeded crop species can be seeded at much greater densities. After seeding, the seeds are then covered with another 2.5 cm layer of vermiculite that is also leveled with a thin straight board. Once seeded, the planting tank is then ready to be irrigated with the nutrient solution. The lower chamber is flooded from the reservoir through portals at one end of the lower chamber. As the lower chamber fills, the water level gradually approaches the perforated metal platform which supports the planting medium. The upper chamber (which contains the planting medium) is eventually flooded to a uniform depth determined by the adjustable float switch that deenergizes the pump when the solution level reaches the desired level. The lower chamber, therefore, serves two purposes. First, it protects the planting medium from swift influx of irrigation solution. Secondly, it allows the irrigation solution to enter the planting medium as a surface (from below) rather than radially from one point source. This prevents the establishment of a herbicide concentration gradient in the planting medium and promotes uniformity of herbicide treatment across the planting tank.

To effectively screen for resistance to a herbicide, one must first establish the threshhold herbicide concentration that will consistently inhibit development of sensitive plants yet allow the development of mutants or variants with significant levels of tolerance or resistance. Pilot studies were conducted that showed a concentration of 100 mg/L of Compound 1 or Compound 12 (used to irrigate the hydroponic system) will consistently stunt or inhibit leaf and root development of wild type soybeans yet allow unifoliolate (but not trifoliolate) formation of mutants that have heritable sulfonylurea tolerance. The same sulfonylurea concentrations would select only highly resistant plants.

Another pilot study demonstrated that sulfonylurea tolerant mutants could be distinguished from wild type when the seeds are densely-planted (12,000 to 13,000 seeds per square meter) in the large hydroponic system when irrigated with a solution containing either 100 or 300 mg/l Compound 12. Hence, the large hydroponics units demonstrate the two key components of the hydroponic screening system: 1) the ability to screen seeds that are planted directly into the hydroponic system which eliminates the labor and time for transplanting established seedlings and 2) the ability to screen densely planted seeds which saves greenhouse space and materials.

Source of Mutagenized Soybean Populations

A sample of eight different M2 populations were screened for SU resistance. These populations differed in either the variety used as starting material, the chemical mutagen used, or the soaking regimes used in the mutagen treatment. All three parental varieties ('Williams', 'Williams 82', and 'A3205') are agronomically acceptable but have herbicide-sensitive ALS activities. A detailed protocol for the generation of one M2 population (A3205-EMS) is outlined to illustrate the general procedure. This is followed by a table listing the variations used to generate the other seven populations.

Approximately 50,000 seeds (8.6 kg) of the variety 'A3205' were poured into a 50 l carboy filled with 45 l of tap water to "pre-soak" the seeds. After 8 h of soaking under continuous aeration, the excess tap water was drained and the swelled seeds were added to a second carboy containing 32 l of 25 mM ethyl methane sulfonate (EMS) in 0.1 M potassium phosphate buffer (pH 5.6). The seeds were then soaked in the presence of the mutagen under continuous aeration for three hours. Treated seeds were washed of exogenous mutagen by first draining the EMS solution and then filling and draining the carboy twice with 30 l of tap water. A third volume of 30 l tap water was added to the carboy and retained as a "post-wash" to soak the seeds for 7 h under continuous aeration. Following the post-wash treatment, seeds were again rinsed with three batches of 20 l tap water. After the final rinse, seeds were decanted onto flat cardboard sheets to drain. After drainage, the seeds were field-planted 2 cm deep in rows spaced 76 cm apart with a density of approximately 30 seeds per meter within the row. The resulting M1 plants were allowed to reach maturity and produce M2 seeds. M2 seeds were harvested, bulked and thoroughly mixed to randomly distribute the progeny of any given M1 plant. Table II lists relevant deviations from the above procedure used to generate the eight M2 populations screened for SU resistance.

TABLE II

MUTAGEN, DOSAGE, SOAKING TIMES, AND POSTWASH TIMES USED TO GENERATE EIGHT DIFFERENT SOYBEAN M2 POPULATIONS

| Population code | Mutagen dose | Exposure time (hours) | Postwash time (hours) | Number of M1 seeds treated | Estimated number of M1 Survivors |
|---|---|---|---|---|---|
| A3205-EMS | 25 mM | 3 | 7 | 50,000 | 40,000 |
| Williams-EMS-1 | 50 mM | 9 | 9 | 10,000 | 7,700 |
| Williams-EMS-2 | 50 mM | 9 | 5 | 10,000 | 7,500 |
| Williams-NMU-1 | 2.5 mM | 3 | 9 | 10,000 | 6,200 |
| Williams 82-NMU-A | 2.5 mM | 5 | 3 | 2,500 | 1,500 |

TABLE II-continued

MUTAGEN, DOSAGE, SOAKING TIMES, AND POSTWASH TIMES USED TO GENERATE EIGHT DIFFERENT SOYBEAN M2 POPULATIONS

| Population code | Mutagen dose | Exposure time (hours) | Postwash time (hours) | Number of M1 seeds treated | Estimated number of M1 Survivors |
|---|---|---|---|---|---|
| Williams 82-NMU-B | 2.5 mM | 5.5 | 2.5 | 2,500 | 1,250 |
| Williams 82-NMU-C | 2.5 mM | 6 | 2 | 2,500 | 1,000 |
| Williams 82-NMU-D 750 | 2.5 mM | 6 | 2 | 2,500 | |

Population code includes (parental variety)-(mutagen)-(numeral or letter code for designated soaking regime).
EMS = ethyl methane sulfonate NMU = nitroso methyl urea Survival rate of M1 plants was based on a visual estimate of percent emergence in field plots or on a subsample of seed observed for emergence frequency.

Table 3 summarizes the results of selection for sulfonylurea resistance within the eight M2 populations. It should be noted that a total of approximately 379,000 M2 individuals were screened for sulfonylurea resistance. Of the eight M2 populations screened, only two (Williams-EMS-2 and Williams-NMU-1) yielded resistant mutants. Examples of selections from these two populations are described herein. Although 21 resistant individuals were selected from the Williams-NMU-1 M2 population, these individuals are probably the result of only one or two mutational events (i.e. the progeny of one or two M1 plants), considering the rarity of dominant mutations. Since all M2 populations were harvested in bulk, it is impossible to make conclusions about mutation frequency. It is also important to note that many putatively "tolerant" mutants were not saved especially after the first putatively "resistant" mutants were selected. Therefore, the number of tolerant versus resistant mutants shown in Table III does not represent the relative frequency of these two types of mutants. The sulfonylurea resistant mutants selected with the applicant's novel hydroponic selection system are the first recorded examples of dominant mutations in soybean; this fact alone testifies to the rarity of such a mutation.

TABLE III

Number and Type of Soybean Mutants Selected from Eight M2 Populations

| Population code | Estimated Number of M2 Plants Screened | Mean number of M2 per M1 plant | Number of Putative Mutants saved Resistant | Tolerant |
|---|---|---|---|---|
| A3205-EMS | 100,000 | 2.5 | 0 | 3 |
| Williams-EMS-1 | 42,000 | 5.4 | 0 | 6 |
| Williams-EMS-2 | 88,000 | 11.7 | 2 | 10 |
| Williams-NMU-1 | 55,000 | 8.9 | 21 | 6 |
| Williams 82-NMU-A | 26,000 | 17.3 | 0 | 2 |
| Williams 82-NMU-B | 30,000 | 24.0 | 0 | 0 |
| Williams 82-NMU-C | 18,000 | 18.0 | 0 | 1 |
| Williams 82-NMU-D | 20,000 | 26.7 | 0 | 1 |

Once true-breeding herbicide resistant mutants were selected from the first round of mutagenesis, a seed increase of such mutants was obtained to generate starting material for a second round of mutagenesis. The intent was to cause a second mutation in the background of a soybean plant that already possessed one mutation for herbicide resistance. The resulting M2 populations were then screened by exposing the population to an herbicide treatment that was lethal to the parental starting material. This screen identified a "second generation" mutant "W4-4" with herbicide resistance greater than that provided by the first mutation alone.

Three different mutant lines (W4, W23, and W28) were shown to contain single dominant mutations for resistance to compound 1 (Table V and Examples 2, 5, and 6). Another mutant line W6 has a similar resistance phenotype (Table IV and Example 9). All four of these lines contain a herbicide resistance mutation that is allelic or closely linked to the W20 mutation (Table V and Examples 2, 5, 6, and 9). This evidence, coupled with the fact that W4, W6, W23, and W28 were all selected from the same small M2 subpopulation as W20 (Table IV), make it highly probable that all five of these mutants are descendents of the same M1 plant (i.e. are identical). Hence, lines W4, W6, W23, and W28 were used as starting material for a second cycle of mutagenesis with the assumption that all four lines were essentially identical to W20 in both genotype and phenotype. Various quantities of seed of each line were mutagenized in a fashion similar to that described above. Significant variations from the A3205 mutagenesis protocol are listed in Table II-A.

TABLE II-A

PROTOCOLS USED FOR SECOND CYCLE OF MUTAGENESIS

| Population code | Mutagen NMU dose | Exposure time (hours) | Postwash time (hours) | Number of M1 seeds treated | Estimated number of M1 Survivors | Number of M2 plants screened |
| --- | --- | --- | --- | --- | --- | --- |
| W4-NMU-T3 | 2.5 mM | 2 | 9 | 12,500 | 5,480 | 73,250 |
| W6-NMU-T3 | 2.5 mM | 2 | 9 | 12,500 | 7,715 | 112,000 |
| W23-NMU-T1 | 2.5 mM | 3 | 5 | 10,000 | 509 | 41,000 |
| W23-NMU-T2 | 2.5 mM | 3 | 8 | 10,000 | 854 | 28,500 |
| W23-NMU-T3A | 2.5 mM | 2 | 9 | 10,000 | 2,720 | 89,250 |
| W23-NMU-T3B | 2.5 mM | 2 | 9 | 14,000 | 7,232 | 75,750 |
| W23-NMU-T1 | 2.5 mM | 3 | 5 | 10,000 | 1,396 | 41,000 |
| W23-NMU-T2 | 2.5 mM | 3 | 8 | 10,000 | 1,815 | 36,750 |
| W23-NMU-T3A | 2.5 mM | 2 | 9 | 10,000 | 2,936 | 120,500 |
| W23-NMU-T3B | 2.5 mM | 2 | 9 | 11,500 | 4,368 | 87,000 |
| TOTAL | | | | 110,500 | 35,025 | 705,000 |

Two screening protocols were used to isolate mutants that had a higher level of herbicide resistance than the previously selected mutants. Both protocols utilized an experimental sulfonylurea (Compound 8) that was toxic to previously selected mutants when sprayed post-emergence at a rate of only 2 g/ha (Table VII). Pilot studies were conducted to discover rates of Compound 8 that would consistently inhibit growth of mutant W20 in both the hydroponic screening system and a seed soak selection system. W20 is a mutant line representative of the class of mutants selected from the first cycle of mutagenesis. W20 contains a single dominant mutation for resistance to many ALS-inhibiting herbicides. By using a screening protocol that uniformly inhibits development of W20, the applicant selected for mutants with herbicide resistance superior even to that of W20 and similar mutants (including W4, W6, W23, and W28).

The first screening protocol used was identical to the "Large-Scale Hydroponic Screening System" described previously except for the fact that 300 ppb of Compound 8 was used as the selective agent instead of 100 ppb of Compound 1. Pilot studies demonstrated that when 300 ppb of Compound 8 was used to irrigate the hydroponic system, W20 seedlings would germinate, emerge, and expand cotyledons but would not develop true leaves. Rare seedlings developing true leaves became very obvious against the background of inhibited seedlings. These rare seedlings were selected as potentially superior to the parental starting material in terms of heritable herbicide resistance.

The second screening protocol was carried out as follows: samples of seed from W20 were tested for preemergence tolerance to Compound 8 by soaking seeds in a 2.0 ppm buffered solution of Compound 8 for 16 hours, rinsing, and planting in flats in a greenhouse. Pilot studies demonstrated that 2 ppm of Compound 8 was sufficient to uniformly inhibit growth of W20 beyond the stage of emergence and cotyledon expansion. Plants developing beyond this stage were selected as potentially superior to the parental starting material in terms of heritable herbicide resistance.

Using these two screening systems, a total of 234 putatively mutant plants were selected from a population of 705,000 M2 plants (Table IIA). Selected plants were transplanted into a standard peat-based soil in 20 cm pots at 7 to 12 days of age. After transplantation, it was obvious that some of the selected plants recovered better than others after exposure to Compound 8. The healthiest-looking plants were suspected of being truly more resistant to Compound 8 than were the mutants with single dominant mutations for sulfonylurea resistance. Leaf samples from the 30 healthiest plant selections were then assayed for their ability to retain in vitro ALS activity in the presence of solutions containing Compound 8 (a potent sulfonylurea) and was compared to that of wild type Williams and previously selected mutant W20. W20 is similar (and probably identical) to mutants W4, W23, and W28 (and presumably W6) in terms of herbicide resistance spectrum (Table VII).

TABLE II-B

RESULTS OF SELECTION FOR RESISTANCE TO COMPOUND 8

| Population code | Number of M2 plants screened | Number of M2 plants selected | Number of plants assayed at ALS level with CMPD 8 | Number of plants with superior ALS resistance to Compound 8 |
| --- | --- | --- | --- | --- |
| W4-NMU-T3 | 73,250 | 15 | 5 | 1 |
| W6-NMU-T3 | 112,000 | 23 | 7 | 0 |
| W23- NMU-T1 | 41,000 | 18 | 0 | 0 |
| W23-NMU-T2 | 28,500 | 15 | 0 | 0 |
| W23-NMU-T3A | 89,500 | 60 | 8 | 0 |
| W23-NMU-T3B | 75,750 | 14 | 4 | 0 |
| W23-NMU-T1 | 41,000 | 17 | 0 | 0 |
| W23-NMU-T2 | 36,750 | 10 | 1 | 0 |
| W23-NMU-T3A | 120,500 | 52 | 5 | 0 |
| W23-NMU-T3B | 87,000 | 10 | 0 | 0 |
| TOTAL | 705,000 | 234 | 30 | 1 |

The present invention is further defined in the following examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various needed usages and conditions.

EXAMPLE 1

Sulfonylurea Resistant Mutant W20

A. Selection

Four Modified Hydropot Solo units were prepared as described in the Detailed Description by filling the planting tanks with a 5 cm layer of pea gravel followed by a 10 cm layer of fine vermiculite. M2 seeds of the William-NMU-1 were densely planted (approx. 16,600 seeds per square meter) by placing the seeds in a single horizontal layer on top of the vermiculite and then covering the seeds with a second level 2.5 cm layer of vermiculite. The nutrient solution reservoir was filled with tap water supplemented with 100 ppb of Compound 1 as the selective agent. Plant tanks were irrigated with the Compound 1 solution for four 30 minute periods per day beginning at 12 midnight, 8 AM, 12 noon, and 4 pm. At twelve days after planting, putative mutant "W20" was selected from one of the Modified Hydropot Solo units based on its vigorous growth in the presence of Compound 1 concentration that was lethal to the surrounding seedlings. The W20 plant was gently removed from the from the hydroponic planting tank and transplanted into a 20 cm pot containing a standard peat-based potting mixture. After transplantation, W20 showed no obvious signs of sulfonylurea injury when compared to wild type. This observation led the applicant to believe that W20 represented a new class of resistant mutants. W20 was allowed to reach maturity under greenhouse conditions and produce an M3 line that was also referred to as W20.

Genetic Stability of Sulfonylurea Resistance in W20

B. Characterization

Thirty M3 seeds of the W20 line were then re-screened for chlorsulfuron resistance by exposing the seeds to 100 ppb Compound 1 using a hydroponic screening system similar to the one described in A. Under these conditions, Compound 1 "sensitivity" was defined as the inability to form leaves, "tolerance" was defined as the ability to form unifoliolate leaves but no subsequent shoot development, "high tolerance" was defined as the ability to form trifoliolates that were somewhat abnormal, and "resistance" was defined as the ability to form both unifoliolate and normal trifoliolate leaves. Twenty-seven of the 30 M3 seeds germinated and all were resistant to Compound 1 (Table IV). Based on this result, the W20 line was classified as homozygous resistant to Compound 1.

Seed Increase of W20 for Future Testing

Another sample of M3 seeds of W20 were field planted and allowed to self-pollinate to increase the number of seeds of the W20 line. In all subsequent repeats where W20 was exposed to Compound 1 or other sulfonylureas, the line showed uniformity in response to the herbicides and was therefore considered nonsegregating or true-breeding for sulfonylurea resistance. All subsequent generations of self-pollinated (inbred) W20 seeds and plants were also referred to as W20. A seed deposit of W20 was made at the American Type Culture Collection (12301 Parklawn Drive, Rockville, Md., 20852) on July 5, 1988. The deposit was identified as ATCC designation 40467.

Inheritance of Sulfonylurea Resistance in W20

Using standard hand pollination procedures, F1 seeds of the cross W20×Williams 82 (wild type) were produced in the field. Five F1 seeds were tested for resistance to Compound 1 by hydroponic exposure to 100 ppb Compound 1 for 19 days. All five F1 seeds and resulting seedlings were resistant to Compound 1 (Table V) indicating that W20's resistance was a dominant trait. After 19 days of exposure to Compound 1, F1 seedlings were transplanted to individual greenhouse pots, allowed to self pollinate and produce F2 seeds. A sample of F2 seeds segregated 22 resistant to 10 sensitive (Table V) when screened hydroponically for Compound 1 reaction. Based on chi-square analysis, this segregation (chi square value=0.67) is not significantly different (at alpha=0.05) from a 3:1 ratio expected for segregation of a single dominant allele. It was therefore concluded that W20's resistance was due to a single dominant mutation conditioning resistance to Compound 1.

EXAMPLE 2

Selection and Characterization of Sulfonylurea Resistant Mutant W4

M2 seeds of the Williams-NMU-1 population were screened for sulfonylurea resistance as described in EXAMPLE 1 except that one of the custom-built large hydroponic units described in the DETAILED DESCRIPTION was used instead of the small modified Hydropot Solo system.

M2 seeds of the Williams-NMU-1 treatment (Table II) were densely planted (approximately 16,600 seeds Per m2) on top of a level 7 cm layer of granular vermiculite supported by the upper chamber of the planting tank of the previously described large hydroponic selection system. The seeds were then covered with a second level 2.5 cm layer of granular vermiculite. The nutrient solution reservoir was then filled with 200 l of a solution containing tap water plus 100 ppb Compound 1. The float valve in the planting tank was adjusted to allow the solution level to reach the upper vermiculite layer. The programmable timer was programmed to enforce four 30-minute soakings of the planting medium per day: 8 to 8:30 AM, 12 noon to 12:30 PM, 4 to 4:30 PM, and 12 midnight to 12:30 AM. The remainder of each day was programmed for drainage and aeration of the planting medium. The irrigation cycle continued for 10 days. At 8 days after planting, the background of wild type seedlings were uniformly inhibited after emergence and expansion of the cotyledons. Putative mutants could have been selected at 8 days after planting, but were kept in the hydroponic system for two more days to help identify the most resistant of the putative mutants. At 10 days after planting, putative mutant "W4" was selected based on its vigorous growth in the presence of the chlorsulfuron concentration that was lethal to the surrounding seedlings. The W4 plant was transplanted and allowed to produce an M3 and subsequent generations of seed as described in EXAMPLE 1. W4 also was resistant to compound 1 based on its ability to grow normally after exposure to normally toxic levels of chlorsulfuron. A seed deposit of W4-4 was made at the American Type Culture Collection (12307 Parklawn Drive, Rockville, Md., 20852) on Sept. 1, 1989. The deposit was identified as ATCC designation 40650.

Genetic stability of W4's Compound 1 resistance and inheritance of W4's resistance were tested as described in Example 1. The results are indicated in Tables IV and V.

Linkage Analysis of Mutant W4 With Mutant W20

Homozygous resistant W4 plants were also crossed with homozygous resistant W20 plants to determine if the mutation in W4 is allelic with, linked with, or at a separate genetic locus than the W20 mutation. This linkage test was conducted by exposing approximately 64 F2 progeny from this cross to 100 ppb of Compound 1 in the large hydroponic screening system. At approximately 8 days after planting, the F2 progeny were scored as either resistant or sensitive to Compound 1. If the two mutants contained mutations at unlinked loci, 1/16 of the F2 progeny l(4 out of 64 plants) would be expected to be sensitive to Compound 1. If the two mutants contained mutations in the same genetic locus or two tightly linked loci, one would expect all F2 progeny to be resistant.

All F2 progeny from the cross between W4 and W20 were resistant to Compound 1 (Table V). This indicates that W4 has a mutation at either the same locus as the W20 mutation or a tightly linked locus. Since W4 was obtained from the same small M2 subpopulation as W20 (Table IV), it is highly likely that W4 and W20 trace back to the same M1 plant and the same mutational event.

EXAMPLE 3

Selection and Characterization of Sulfonylurea Resistant Mutant W17

Mutant "W17" was selected from the Williams-NMU-1 M2 population the same as W20 as described in EXAMPLE 1. Seed of the W17 line was increased as described for W20 in EXAMPLE 1.

Genetic stability of W17's chlorsulfuron resistance and inheritance of W17's resistance were tested as described in EXAMPLE 1.

The results are indicated in Tables IV and V.

Linkage Analysis of Mutant W17 With Mutant W20

Homozygous resistant W17 plants were also crossed with homozygous resistant W20 plants to determine if the mutation in W17 is allelic with, linked with, or at a separate genetic locus than the W20 mutation. This linkage test was conducted by exposing approximately 64 F2 progeny from this cross to 100 ppb of Compound 1 in the large hydroponic screening system. At approximately 8 days after planting, the F2 progeny were scored as either resistant or sensitive to Compound 1. If the two mutants contained mutations at unlinked loci, 1/16 of the F2 progeny (4 out of 64 plants) would be expected to be sensitive to Compound 1. If the two mutants contained mutations in the same genetic locus or two tightly linked loci, one would expect all F2 progeny to be resistant.

All F2 progeny from the cross between W17 and W20 were resistant to Compound 1 (Table V). This indicates that W17 has a mutation at either the same locus as the W20 mutation or a tightly linked locus. Since W17 was obtained from the same small M2 subpopulation as W20 (Table IV), it is highly likely that W17 and W20 trace back to the same M1 plant and the same mutational event.

EXAMPLE 4

Selection and Characterization of Sulfonylurea Resistant Mutant W19

Mutant "W19" was selected from the Williams-NMU-1 M2 population the same as W20 as described in EXAMPLE 1. Seed of the W19 line was increased as described for W20 in EXAMPLE 1.

Genetic stability of W19's chlorsulfuron resistance, inheritance of W19's resistance were tested as described in EXAMPLE 1. The results are indicated in Tables IV and V.

Linkage Analysis of Mutant W19 With mutant W20

Homozygous resistant W19 plants were also crossed with homozygous resistant W20 plants to determine if the mutation in W19 is allelic with, linked with, or at a separate genetic locus than the W20 mutation. This linkage test was conducted by exposing approximately 64 F2 progeny from this cross to 100 ppb of Compound 1 in the large hydroponic screening system. At approximately 8 days after planting, the F2 progeny were scored as either resistant or sensitive to Compound 1. If the two mutants contained mutations at unlinked loci, 1/16 of the F2 progeny (4 out of 64 plants) would be expected to be sensitive to Compound 1. If the two mutants contained mutations in the same genetic locus or two tightly linked loci, one would expect all F2 progeny to be resistant.

All F2 progeny from the cross between W19 and W20 were resistant to Compound 1 (Table V). This indicates that W19 has a mutation at either the same locus as the W20 mutation or a tightly linked locus. Since W19 was obtained from the same small M2 subpopulation as W20 (Table IV), it is highly likely that W19 and W20 trace back to the same M1 plant and the same mutational event.

EXAMPLE 5

Selection and Characterization of Sulfonylurea Resistant Mutant W23

Mutant "W23" was selected from the Williams-NMU-1 M2 population the same as W20 as described in EXAMPLE 1. Seed of the W23 line was increased as described for W20 in EXAMPLE 1.

Genetic stability of W23's chlorsulfuron resistance and inheritance of W23's resistance were tested as described in EXAMPLE 1.

The results are indicated Tables IV and V.

Linkage Analysis of Mutant W23 With Mutant W20

Homozygous resistant W23 plants were also crossed with homozygous resistant W20 plants to determine if the mutation in W23 is allelic with, linked with, or at a separate genetic locus than the W20 mutation. This linkage test was conducted by exposing approximately 64 F2 progeny from this cross to 100 ppb of Compound 1 in the large hydroponic screening system. At approximately 8 days after planting, the F2 progeny were scored as either resistant or sensitive to Compound 1. If the two mutants contained mutations at unlinked loci, 1/16 of the F2 progeny (4 out of 64 plants) would be expected to be sensitive to Compound 1. If the two mutants contained mutations in the same genetic locus or two tightly linked loci, one would expect all F2 progeny to be resistant.

All F2 progeny from the cross between W23 and W20 were resistant to Compound 1 (Table V). This indicates that W23 has a mutation at either the same locus as the W20 mutation or a tightly linked locus. Since W23 was obtained from the same small M2 subpopulation as W20 (Table IV), it is highly likely that W23 and W20 trace back to the same M1 plant and the same mutational event.

EXAMPLE 6

Selection and Characterization of Sulfonylurea Resistant Mutant W28

Mutant "W28" was selected from the Williams-NMU-1 M2 population the same as W20 as described in EXAMPLE 1. Seed of the W28 line was increased as described for W20 in EXAMPLE 1.

Genetic stability of W28's chlorsulfuron resistance and inheritance of W28's resistance were tested as described in EXAMPLE 1.

The results are indicated in Tables IV and V.

Linkage Analysis of Mutant W28 With Mutant W20

Homozygous resistant W28 plants were also crossed with homozygous resistant W20 plants to determine if the mutation in W28 is allelic with, linked with, or at a separate genetic locus than the W20 mutation. This linkage test was conducted by exposing approximately 64 F2 progeny from this cross to 100 ppb of Compound 1 in the large hydroponic screening system. At approximately 8 days after planting, the F2 progeny were scored as either resistant or sensitive to Compound 1. If the two mutants contained mutations at unlinked loci, 1/16 of the F2 progeny (4 out of 64 plants) would be expected to be sensitive to Compound 1. If the two mutants contained mutations in the same genetic locus or two tightly linked loci, one would expect all F2 progeny to be resistant.

All F2 Progeny from the cross between W28 and W20 were resistant to Compound 1 (Table V). This indicates that W28 has a mutation at either the same locus as the W20 mutation or a tightly linked locus. Since W28 was obtained from the same small M2 subpopulation as W20 (Table IV), it is highly likely that W28 and W20 trace back to the same M1 plant and the same mutational event.

EXAMPLE 7

Selection of Sulfonylurea Resistant Mutant W36

Mutant "W36" was selected from the Williams-EMS-2 M2 population the same as W20 was selected from the Williams-NMU-1 M2 population as described in EXAMPLE 1. M3 seed of the W36 line was increased as described for W20 in EXAMPLE 1.

Genetic Stability of Sulfonylurea Resistance in W36

Genetic stability of W36's chlorsulfuron resistance was tested as W20 in Example 1 except that different results were obtained as shown in Table IV. The W36 M3 line (derived from the self-pollinated W36 M2 selection) segregated 25 resistant to 5 sensitive. This segregation ratio is not significantly different than a 3:1 ratio expected for segregation of a single dominant allele for chlorsulfuron resistance. It was therefore concluded that the original M2 selection of W36 was heterozygous for a single dominant mutation conferring chlorsulfuron resistance.

Establishment of the W36 Mutation in the Homozygous Condition

A sample of the M3 family of W36 was field-planted as described in EXAMPLE 1. Instead of harvesting the M3 plants in bulk (as done for homozygous mutants such as W20), individual M3 plants were harvested and the resulting M4 families were kept separate. A 15 to 20 seed sample of each of 100 M4 families was then screened for resistance to 100 ppb chlorsulfuron using the large hydroponics unit as described in Example 2. In this case, however, each M4 family was planted in a defined area within the planting tank so that the response of each M4 family could be monitored. Remnant seed of the M4 families that were uniformly resistant to chlorsulfuron (homozygous for the W36 mutation) were then bulked to reconstitute the W36 line in a condition that was homozygous and true-breeding for the chlorsulfuron resistance mutation.

Linkage Analysis of Mutant W36 With Mutant W20

Homozygous resistant W36 plants were crossed with homozygous resistant W20 plants to determine if the mutation in W36 is allelic with, linked with, or at a separate genetic locus than the W20 mutation. This linkage test was conducted by exposing approximately 60 F2 progeny from this cross to 100 ppb of Compound 1 in the large hydroponic screening system. At approximately 8 days after planting, the F2 progeny were scored as either resistant or sensitive to Compound 1. If the two mutants contained mutations at unlinked loci, 1/16 of the F2 progeny (approximately 4 out of 60 plants) would be expected to be sensitive to Compound 1. If the two mutants contained mutations in the same genetic locus or two tightly linked loci, one would expect all F2 progeny to be resistant.

All F2 progeny from the cross between W36 and W20 were resistant to Compound 1 (Table V). This indicates that W36 has a mutation at either the same locus as the W20 mutation or a tightly linked locus. Although the two mutations may be similar or even identical, they were induced independently since W36 was obtained from a different M2 subpopulation than W20 (Table IV).

EXAMPLE 8

Selection of Sulfonylurea Resistant Mutant W40

Mutant "W40" was selected from the Williams-EMS-2 M2 population the same as W20 was selected from the Williams-NMU-1 M2 population as described in EXAMPLE 1. M3 Seed of the W40 line was increased as described for W20 in EXAMPLE 1.

Linkage Analysis of Mutant W40 With Mutant W20

Homozygous resistant W40 plants were crossed with homozygous resistant W20 plants to determine if the mutation in W40 is allelic with, linked with, or at a separate genetic locus than the W20 mutation. This linkage test was conducted by exposing approximately 54 F2 progeny from this cross to 100 ppb of Compound 1 in the large hydroponic screening system. At approximately 8 days after planting, the F2 progeny were scored as either resistant or sensitive to Compound 1. If the two mutants contained mutations at unlinked loci, 1/16 of the F2 progeny (approximately 3 out of 54 plants) would be expected to be sensitive to Compound 1. If the two mutants contained mutations in the same genetic locus or two tightly linked loci, one would expect all F2 progeny to be resistant.

Out of the 54 F2 progeny from the cross between W40 and W20, 4 were sensitive to Compound 1 (Table V). Four sensitive plants out of 54 is extremely close to the expected theoretical ratio for segregation of two unlinked dominant genes. This indicates that W40 has a mutation at a different locus than the W20 mutation. Although 54 plants do not provide enough data to claim independent segregation of the two loci, W40 defines the existence of a second soybean locus that controls reaction to sulfonylurea herbicides. The fact that the W40 mutation resides at a separate locus than the W20 mutation provides the opportunity to breed plants with herbicide resistance genes at both loci. Presumably such plants could have a level of herbicide resistance that is superior to that of either single mutant.

Genetic Stability of Sulfonylurea Resistance in W40

Genetic stability of W40's chlorsulfuron resistance was tested as described for W20 in EXAMPLE 1 except that different results were obtain as shown in Table IV. The W40 M3 line (derived from the self-pollinated W40 M2 selection) segregated 20 resistant to 8 sensitive. This segregation ratio is not significantly different than a 3:1 ratio expected for segregation of a single dominant mutation conferring chlorsulfuron resistance.

Establishment of the W40 Mutation in the Homozygous Condition

W40 was obtained in a condition homozygous for its dominant chlorsulfuron resistance mutation in the same way as described for mutant W36 in EXAMPLE 7.

TABLE IV

M3 Family Segregation for Compound 1
Reaction of Resistant and Tolerant Soybean Mutants

| M2 Plant | M2 Population | M3 Segregation R,Ht,T,S | Chi-square value for 3:1 | Classification of M2 Plant | | |
|---|---|---|---|---|---|---|
| | | | | Genotype | Phenotype | Gene Action |
| W2 | WM EMS-2 | 0,0,3,0 | | ? | TOL | ? |
| W4 | WM NMU-1 | 8,0,0,0 | | HOMO | RESIST | ? |
| W5 | WM NMU-1 | 11,15,0,4 | 2.18 | HETERO | RESIST | DOM |
| W6 | WM NMU-1 | 17,3,0,0 | | HOMO | RESIST | ? |
| W7 | WM EMS-1 | 0,0,12,0 | | HOMO | TOL | ? |
| W12 | WM NMU-1 | 12,20,0,8 | 0.53 | HETERO | RESIST | DOM |
| W13 | WM NMU-1 | 16,21,0,8 | 1.25 | HETERO | RESIST | DOM |
| W14 | WM NMU-1 | 16,25,0,15 | 0.10 | HETERO | RESIST | DOM |
| W15 | WM NMU-1 | 23,21,0,11 | 0.73 | HETERO | RESIST | DOM |
| W16 | WM NMU-1 | 0,19,11,16 | 2.35 | HETERO | RESIST | DOM |
| W17 | WM NMU-1 | 26,0,0,0 | | HOMO | RESIST | ? |
| W18 | WM NMU-1 | 12,26,0,12 | 0.03 | HETERO | RESIST | DOM |
| W19 | WM NMU-1 | 29,0,0,0 | | HOMO | RESIST | ? |
| W20 | WM NMU-1 | 27,0,0,0 | | HOMO | RESIST | ? |
| W21 | WM NMU-1 | 0,8,27,0 | | HOMO | TOL | ? |
| W22 | WM NMU-1 | 0,0,52,0 | | HOMO | TOL | ? |
| W23 | WM NMU-1 | 19,24,0,0 | | HOMO | RESIST | ? |
| W24 | WM NMU-1 | 19,16,0,17 | 1.64 | HETERO | RESIST | DOM |
| W25 | WM NMU-1 | 0,0,38,0 | | HOMO | TOL | ? |
| W26 | WM NMU-1 | 6,32,0,7 | 2.14 | HETERO | RESIST | DOM |
| W27 | WM NMU-1 | 0,18,5,4 | 1.49 | HETERO | TOL | DOM |
| W28 | WM NMU-1 | 30,15,0,0 | | HOMO | RESIST | ? |
| W29 | WM NMU-1 | 0,0,34,0 | | HOMO | TOL | ? |
| W30 | WM NMU-1 | 28,20,5,0 | | HOMO | RESIST | ? |
| W31 | WM NMU-1 | 20,18,0,15 | 0.31 | HETERO | RESIST | DOM |
| W32 | WM NMU-1 | 28,19,4,0 | | HOMO | RESIST | ? |
| W33 | WM NMU-1 | 28,21,4,0 | | HOMO | RESIST | ? |
| W34 | WM NMU-1 | 20,18,0,13 | 0.01 | HETERO | RESIST | DOM |
| W35 | WM NMU-1 | 16,16,1,13 | 0.26 | HETERO | RESIST | DOM |
| W36 | WM EMS-2 | 25,0,0,5 | 1.11 | HETERO | RESIST | DOM |
| W37 | WM EMS-2 | 0,30,20,0 | | HOMO | TOL | ? |
| W39 | WM EMS-2 | 0,21,0,9 | 0.40 | HETERO | TOL | DOM |
| W40 | WM EMS-2 | 20,0,0,8 | 0.19 | HETERO | RESIST | DOM |
| W41 | WM EMS-2 | 0,29,0,0 | | HOMO | TOL | ? |
| W42 | WM EMS-2 | 0,23,2,0 | | HOMO | TOL | ? |
| W43 | WM EMS-2 | 0,28,1,0 | | HOMO | TOL | ? |
| W44 | WM EMS-2 | 0,29,0,0 | | HOMO | TOL | ? |
| W45 | WM EMS-2 | 0,16,14,0 | | HOMO | TOL | ? |
| W46 | WM EMS-2 | 0,23,6,0 | | HOMO | TOL | ? |
| W48 | WM EMS-2 | 0,1,24,0 | | HOMO | TOL | ? |
| W48 | WM EMS-2 | 0,24,0,0 | | HOMO | TOL | ? |
| W50 | WM EMS-2 | 0,29,0,0 | | HOMO | TOL | ? |
| W52 | WM EMS-2 | 0,0,25,0 | | HOMO | TOL | ? |
| W53 | WM EMS-2 | 0,7,18,0 | | HOMO | TOL | ? |
| W55 | WM EMS-2 | 0,7,22,0 | | HOMO | TOL | ? |
| W56 | WM 82 NMU-A | 0,0,13,0 | | HOMO | TOL | ? |
| W57 | WM 82 NMU-A | 0,0,26,0 | | HOMO | TOL | ? |
| W60 | WM 82-NMU-C | 0,0,24,0 | | HOMO | TOL | ? |
| W62 | WM 82-NMU-D | 0,0,18,0 | | HOMO | TOL | ? |
| A1 | A3205 EMS | 0,8,7,0 | | HOMO | TOL | ? |
| A2 | A3205 EMS | 0,0,8,0 | | HOMO | TOL | ? |

TABLE IV-continued

M3 Family Segregation for Compound 1
Reaction of Resistant and Tolerant Soybean Mutants

| M2 Plant | M2 Population | M3 Segregation R,Ht,T,S | Chi-square value for 3:1 | Classification of M2 Plant | | |
|---|---|---|---|---|---|---|
| | | | | Genotype | Phenotype | Gene Action |
| A3 | A3205 EMS | 0,0,1,0 | ? | ? | TOL | ? |

R = resistant
Ht = highly tolerant (an intermediate class)
T = tolerant
S = sensitive to chlorsulfuron at 100 mg L-1 in hydroponics
Chi-square values of less than 3.84 indicate that observed segregation ratio is not significantly different than 3:1 at alpha = 0.05. Ht and/or T individuals were pooled with R individuals for chi-square testing of segregating families.
HOMO = homozygous/true breeding
HETERO = heterozygous/segregating progeny
? = not enough data
DOM = resistance or tolerance is segregating as a dominant allele at a single locus
? = no segregation data

TABLE V

Compound 1 Reaction of F1 and F2 Progenies From
Crosses Between Chlorsulfuron Resistant (Mutant)
and Chlorsulfuron Sensitive (Williams 82) Soybean Lines

| | Number of Plants | | Chi-square Value* | |
|---|---|---|---|---|
| Line or Cross | Resistant or Highly Tolerant | Sensitive | for Fit to 3:1 Ratio or 15:1 in Segregating F2 Progenies | |
| Williams 82 | 0 | 4 | 3:1 | 15:1 |
| W4 | 33 | 0 | 0.10 | 3.33 |
| W4 × Williams 82 F1 | 4 | 0 | | |
| W4 × Williams 82 F2 | 23 | 8 | | |
| W4 × W20 F2*** | 63 | 0 | | |
| W17 | 30 | 0 | 4.77* | 0.04 |
| W17 × Williams 82 F1 | 2 | 0 | | |
| W17 × Williams 82 F2 | 26 | 2 | | |
| W17 × W20 F2*** | 61 | 0 | | |
| W19 | 26 | 0 | 0.49 | 32.58** |
| W19 × Williams 82 F1 | 1 | 0 | | |
| W19 × Williams 82 F2 | 23 | 10 | | |
| W19 × W2 F2*** | 64 | 0 | | |
| W20 | 29 | 0 | 0.67 | 34.13** |
| W20 × Williams 82 F1 | 5 | 0 | | |
| W20 × Williams 82 F2 | 22 | 10 | | |
| W23 | 33 | 0 | 3.89 | 0.62 |
| W23 × Williams 82 F1 | 1 | 0 | | |
| W23 × Williams 82 F2 | 28 | 3 | | |
| W23 × W20 F2*** | 66 | 0 | | |
| W28 | 35 | 0 | 0.89 | 30.04** |
| W28 × Williams 82 F1 | 1 | 0 | | |
| W28 × Williams 82 F2 | 16 | 8 | | |
| W28 × W20 F2*** | 66 | 0 | | |
| W6 × W20 F2 | 57 | 0 | 8.92** | 0.12 |
| W36 × W20 F2*** | 60 | 0 | | |
| W40 × W20 F2*** | 50 | 4 | | |

*At a = 0.05, a chi-square value of 3.84 is significant.
**At a = 0.025, a chi-square value of 5.02 is significant.
***This F2 data includes pooled data from the reciprocal cross also.

EXAMPLE 9

Selection and Characterization of Sulfonylurea Resistant Mutant W6

Mutant "W6" was selected from the Williams-NMU-1 M2 population the same as W4 as described in Example 2. Genetic stability of W6.s chlorsulfuron resistance was tested as described in Example 1. Since none of the M3 seeds from W6 were sensitive to chlorsulfuron (Table IV), W6 appears to breed true for resistance to chlorsulfuron. Since W6 was selected from the same M2 population as W4, W17, W19, W20, W23, and W28 (which probably trace back to the same mutational event), it was presumed that W6 was similar to W20 in both genotype and herbicide resistance phenotype. Although W6 was not crossed to wild type Williams plants to confirm monogenic inheritance, the probability of W6 containing any more than a single mutation for sulfonylurea resistance is extremely small. This assumption coupled with the following linkage test provide strong evidence that W6 is identical to W20 in terms of herbicide resistance.

Linkage Analysis of Mutant W6 With Mutant W20

Homozygous resistant W6 plants were crossed with homozygous resistant W20 plants to determine if the mutation in W6 is allelic with, linked with, or at a separate genetic locus than the W20 mutation. This linkage test was conducted by exposing approximately 57 F2 progeny from this cross to 300 ppb of Compound 1 in the large hydroponic screening system. At approximately 14 days after planting, the F2 progeny were scored as either resistant or sensitive to Compound 1. If the two mutants contained mutations at unlinked loci, 1/16 of the F2 progeny (4 out of 64 plants) would be expected to be sensitive to Compound 1. If the two mutants contained mutations in the same genetic locus or two tightly linked loci, one would expect all F2 progeny to be resistant.

All F2 progeny from the cross between W6 and W20 were resistant to Compound 1 (Table V). This indicates that W6 has a mutation at either the same locus as the W20 mutation or a tightly linked locus. Since W6 was obtained from the same small M2 subpopulation as W20 (Table IV), it is highly likely that W6 and W20 trace back to the same M1 plant and the same mutational event.

EXAMPLE 10

Selection and Characterization of Mutant W4-4

Approximately 25,000 M2 seeds (4500 grams) from each of three M2 populations (W4-NMU-T3, W6-NMU-T3, and W23-NMU-T3B) were screened for resistance to Compound 8 using a seed soak selection procedure similar to that described in CR-8362. Each population sample was placed in a separate immersible mesh bag. The bags were then immersed and soaked for 16 hours in an aqueous solution containing 2 ppm of Compound 8. The solution was kept under continuous aeration through the use of an "air stone" supplied with air from a standard aquarium pump. During the soaking period, the seeds imbibed both water and the dissolved herbicide. After the soaking period, the seeds were washed in running tap water for two minutes to remove exogenous herbicide solution. The applicant employed existing greenhouse pallets with flat horizontal surfaces constructed from a perforated metal grating which allowed for excellent drainage. The metal grating was then covered with a single layer of cheese cloth to prevent soil from falling through the perforations. A planting bed was created by filling the greenhouse pallets with a peat-based soil mixture. The soil mixture was leveled at 7 cm deep by dragging a flat board across the surface of the mixture. Prior to planting, the 7 cm soil mixture layer was thoroughly moistened by sprinkling the upper surface with tap water. Excess water drained through the perforated greenhouse bench. The herbicide-treated seeds were then planted out in a single horizontal layer at a density of approximately 12,000 seeds per square meter on the level planting bed. The seeds were then covered with a 2.5 cm level layer of coarse vermiculite. The described planting medium was kept moist by periodically sprinkling the upper surface of the planting medium with plain tap water. At 8 days after planting, all of the viable seeds had germinated, emerged and expanded their cotyledons. However, only a few of the seedlings had proceeded to develop true leaves. These few seedlings were easily detectable because of the presence of their leaves against a background of uniformly inhibited seedlings. The healthiest looking seedlings were selected and transplanted into separate 20 cm pots. Selected seedlings were named according to the parental source material and the order in which the were selected. Individual M2 plant selections from this screen included W4-4, W4-5, and W4-6 from the W4-NMU-T3 population; W6-1, W6-2, W6-3, and W6-4 from the W6-NMU-T3 population; and W23-9, W23-10, and W23-11 from the W23-NMU-T3B population.

At approximately 1 month after transplantation, some of the selections appeared much healthier than others. For example, W4-4, W4-6, W6-1, W6-2, W6-4, W23-10, and W23-11 recovered very well from the seed soak treatment with Compound 8. These plants were suspected of having a higher level of ALS resistance to Compound 8 than did the parental material from which they were derived. The applicant was also interested to see if any of these selections were cross resistant to an imidazolinone herbicide such as Compound 9. To test this hypothesis, leaf tissue of the one-month-old M2 plants was sampled and assayed in vitro for ALS activity in the presence of Compound 8 and Compound 9. The ALS assay procedure was essentially identical to the previously described ALS assay except that the herbicide concentrations tested were 100 ppb Compound 8 and 10 ppm Compound 9. Williams and mutant W20 soybean plants were also assayed as control genotypes for comparison. Williams contains no genes conferring the ALS-based sulfonylurea resistance while W20 is homozygous for a single mutation conferring ALS-based sulfonylurea resistance.

At the ALS enzyme level, only mutant W4-4 appears to be significantly more resistant than W20 to Compounds 8 and 9 (Table V-A).

TABLE V-A

| Genotype | Percentage of ALS Activity Remaining in the Presence of Compounds 8 and 9 | |
|---|---|---|
|  | Compound 8 100 ppb | Compound 9 10 ppm |
|  | uninhibited ALS activity as % of control | |
| Williams | −0.3 | 14.0 |
| W20 | 10.7 | 18.4 |
| W4-4 | 37.6* | 44.3* |
| W4-5 | 7.1 | 19.3 |
| W4-6 | 4.0 | 10.7 |
| W6-1 | 8.5 | 16.2 |
| W6-2 | 9.7 | 11.7 |
| W6-4 | 10.5 | 18.7 |
| W23-10 | 7.9 | 19.5 |
| W23-11 | 3.8 | 13.0 |
| LSD (0.05) | 2.9 | 5.1 |

*Significantly higher ALS resistance than W20.

Production of a True-breeding Resistant W4-4 Line

The original W4-4 M2 plant was allowed to self pollinate, mature, and produced a family of M3 seeds. An M3 progeny test was then conducted to determine if the new resistance phenotype was heritable and if the M3 family was true-breeding or segregating for the new resistance trait. The M3 progeny of W4-4 were screened for resistance with the same seed soak technique used to select the original W4-4 M2 plant. Twenty seeds each of the W4-4 M3 family, W20 line, and Williams line were soaked for 16 hours in a solution of 2 ppm of Compound 8. Twenty additional seeds of Williams were soaked for 16 hours in plain tap water as a control treatment. Treated seeds were then washed for two minutes in running water. Each seed was then planted in a separate pot for ease of observation. Within two weeks of planting, it was observed that all of the Williams and W20 plants had emerged and expanded cotyledons but had not started to form true leaves. However, all twenty W4-4 plants had developed both unifoliolate and trifoliolate leaves and were essentially identical to the control plants in vigor. This demonstrated that the W4-4 resistance phenotype was heritable and clearly superior to the W20 resistance phenotype. The uniform resistance of all M3 progeny demonstrated that the original W4-4 M2 plant was homozygous for the new resistance mutation and that the new line of W4-4 plants were true-breeding for the new resistance phenotype.

Utility

The new class of sulfonylurea-resistant soybean mutants can now be used as a source of herbicide resistance in soybean breeding programs. Since the mutations are present in an acceptable agronomic background (Williams), the monogenic dominant resistance can be transferred quickly and efficiently through conventional means without sacrificing agronomic traits or without the need for extensive backcrossing. The use of sulfonylurea-resistant soybean varieties will greatly expand the utility of sulfonylurea herbicides and provide the soybean farmer with more options for weed control; herbicides previously excluded from soybean application (due to poor crop safety) could be used for soybean weed control. Sulfonylurea resistance will also increase the safety margin for application of sulfonylurea herbicides that are currently registered for use on soybean. With less concern for crop safety constraints, sulfonylurea resistance also provides an opportunity to combine herbicides that have complementary weed control spectrums to enable the farmer to control additional weed species.

Dominant sulfonylurea herbicide resistance could also be used to produce experimental or commercial quantities of pure F1 hybrid seeds. In such an application, a herbicide-resistant line (that is rendered male sterile through genetic, chemical, and/or manual means) can be planted (either interplanted or in separate rows) in the same field with a male fertile but herbicide sensitive line. After pollination, the male parent can be removed from the field with a sulfonylurea herbicide treatment that is selectively lethal to the male parent. The entire field (containing F1 seeds borne by the sulfonylurea-resistant female line) can then be bulk harvested without seed contamination from the male line.

Dominant sulfonylurea resistance could also be a useful tool in the experimental or commercial production of F2 varieties. In such an application, F1 hybrid seed would be produced on a herbicide sensitive female parent (that could be rendered at least partially male sterile through genetic, chemical, and/or manual means) that is fertilized by pollen from a parent with dominant homozygous herbicide resistance. Male and female parents would be planted in separated rows to facilitate mechanical harvest of seed from the female parent. Since the resulting F1 seeds/plants will be herbicide resistant (heterozygous), undesirable seeds/plants resulting from self-pollination of the female parent can then be rogued from a population of F1 seeds/plants with a herbicide treatment that is selectively lethal to the sensitive female line. This would result in a pure stand of F1 plants that could be bulk harvested for the production of a pure F2 seed population.

A selectively lethal sulfonylurea treatment could be used to rogue sensitive plants from sulfonylurea-resistant populations that have been contaminated through careless seed handling operations. Currently, the use of other dominant markers (such as purple hypocotyls and tawny pubescence) requires visual inspection of each plant for expression of the marker and hand roguing of undesirable types. Such labor makes these visual markers impractical for commercial-scale purification of inbred lines or hybrids. With dominant herbicide resistance, large seed production fields can be easily rogued by spraying the entire field with a herbicide treatment that is lethal to herbicide-sensitive plants.

Demonstration of Resistance to Postemergence Chlorsulfuron Application and Cross-Resistance to Other Sulfonylureas In addition to isolation and confirmation of heritable sulfonylurea resistance, the hydroponic screen demonstrated resistance to preemergence application of Compound 1. Subsequent tests were conducted to demonstrate resistance of true breeding mutant lines (M3 families) to foliar (postemergence) applications of Compound 1 and other sulfonylurea herbicide compounds (see Table I). The following examples are representative of tests that repeatedly confirm the sulfonylurea resistance phenotype of soybean mutants isolated using the applicant's hydroponic selection technique.

Test A

In the first post-emergence test, two true-breeding resistant mutant lines, W19 and W20, were compared to previously isolated tolerant mutants and wild-type Williams 82. Eighteen pots (20 cm diameter) of each soybean line (2 seeds per pot) were planted using a standard sterile potting mix. When the seedlings reached the second trifoliolate stage, plants were thinned back to one plant per pot. Each pot was then sprayed with a specific herbicide treatment using a conveyor belt spray apparatus to emulate field application. The nine different herbicide treatments included one rate (8 g/ha) of Compound 1 and two rates (8 and 32 g/ha) each of four other sulfonylurea herbicides (Compounds 2,3,7 and 8) (see Table VI) using a factorial treatment design with 2 replications.

TABLE VI

Comparison of "Williams 82", Mutant 1-184A, and New Mutants W19 and W20 in Terms to response to Postemergence Application of Five Sulfonylurea Herbicides

TABLE VI

| | | Comparison of "Williams 82", Mutant 1-184A, and New Mutants W19 and W20 in Terms to response to Postemergence Application of Five Sulfonylurea Herbicides | | | |
|---|---|---|---|---|---|
| Herbicide | g/ha | WM 82 | 1-184A | W19 | W20 | LSD (0.05) |
| CMPD 1 | 8 | 97 | 97 | 12 | 13 | 5 |
| CMPD 2 | 8 | 13 | 13 | 0 | 0 | 11 |
| | 32 | 63 | 58 | 7 | 6 | 11 |
| CMPD 3 | 8 | 92 | 90 | 14 | 8 | 6 |
| | 32 | 95 | 91 | 63 | 63 | 6 |
| CMPD 7 | 8 | 95 | 93 | 65 | 65 | 19 |
| | 32 | 93 | 93 | 80 | 84 | 19 |
| CMPD 8 | 8 | 95 | 93 | 84 | 93 | 8 |
| | 32 | 95 | 92 | 95 | 97 | 8 |

Mean % injury = average injury of two replications rated at 3 dates.

Test B

In the second postemergence test, six true-breeding resistant mutant lines (W4, W17, W19, W20, W23, and W28) were compared to Williams 82 for cross resistance to a broad range of ALS inhibitors including eight sulfonylureas and three imidazolinones. Two seeds were planted in each 10 cm pot and allowed to grow to the second trifoliolate stage. Pots were not thinned back if both plants were at the proper stage. For each of 11 herbicides, two rates (Table VII) were selected based on previous data: the low rate was expected to cause significant injury (but not death) to Williams 82 and the high rate was expected to severely injure or kill Williams 82. All but a few line x rate treatments were replicated twice.

In both postemergence tests, plants were returned to the greenhouse after treatment and provided with ample light, moisture, and nutrients to support healthy plant growth. At regular intervals (7 to 12 days), each pot was rated for percent herbicide injury according to the scale shown in Table VIII. Two to three ratings per pot were recorded over a three-week period and averaged to obtain a single value for each pot For each herbicide, analysis of variance on injury ratings was performed separately. Fisher's least significant difference (LSD) was used to determine the significance of line mean differences at each herbicide rate using the 95% level of confidence.

"Resistance" was defined as "the ability to survive, with agronomically acceptable injury, a concentration of herbicide that is normally lethal or extremely injurious to individuals of a given species".

Based on herbicide trials, at 1 to 3 weeks after treatment, 30% injury (according to Table VIII) is generally considered the threshhold between commercially acceptable and unacceptable levels of soybean injury. For the purpose of interpreting the postemergence herbicide test results, a soybean line was considered "resistant" to a particular treatment if less than 30% injury was observed during the first 3 weeks after application. If injury was greater than 30% but significantly less than the injury displayed by wild-type soybean plants, the soybean line was considered more "tolerant" of that treatment than wild-type.

Previously isolated mutants were not significantly different from Williams 82 in terms of reaction to postemergence treatment of the tested sulfonylurea herbicides. However, it is clear that mutants W19 and W20 (representatives of the new class of mutants) are resistant to postemergence rates of Compounds 1, 2 and 3 that severely injure or kill both Williams 82 and 1-184A. Postemergence sulfonylurea resistance can clearly be used to differentiate the new class of resistant soybean mutants from the previously isolated sulfonylurea-tolerant soybean mutants. W19 and W20 were also more tolerant than Williams 82 of postemergence application of Compound 7 at 8 g/ha. Obviously, these mutants do not display the same level of resistance to all sulfonylureas. Rates of Compound 7 and Compound 8 were decreased for the subsequent test to study the resistance phenotype at rates that are sublethal to wild-type soybeans.

From the results of the second post-emergence test (Table VII), it is clear that all mutant lines possess a higher level of tolerance or resistance (compared to Williams 82) to all postemergence sulfonylurea treatments. These mutants, however, are not more tolerant of the imidazolinones, Compounds 9, 10, and 11 than Williams 82. In response to the third imidazolinone, Compound 11, only mutants W17, W19, and W20 were slightly more tolerant than Williams 82. Apparently, the resistance afforded by these mutants is not equally effective against all ALS inhibitors. Within the sulfonylurea herbicides, there is considerable variation in the degree of resistance or tolerance afforded by these mutants. The six mutants studied seem to be very similar in reaction to the herbicides tested. Since all six were selected from the same M2 population, these mutants may trace back to the same mutational event (same M12 plant).

TABLE VII

Responses of "Williams 82" and Mutant Soybean Lines to Eight Sulfonylurea and Three Imidazolinone Herbicides Applied Post-emergence at Second Trifoliolate Stage

| Herbicide | Rate g/ha | Wm 82 | W4 | W17 | W19 | W20 | W23 | W28 | LSD (0.05) |
|---|---|---|---|---|---|---|---|---|---|
| | | | | mean % injury | | | | | |
| CMPD 1 | 2 | 98 | 0 | 0 | 0 | —[a] | —[a] | 0 | —[a] |
| | 8 | 100 | 0 | 0 | 13 | 0 | 0 | 0 | —[a] |
| CMPD 2 | 16 | 70 | 0 | 0 | 0 | 5 | 0 | 0 | 28 |
| | 64 | 91 | 5 | 3 | 6 | 5 | 8 | 5 | 28 |
| CMPD 3 | 2 | 60 | 3 | 0 | 5 | 0 | 0 | 8 | 18 |
| | 8 | 94 | 18 | 25 | 29 | 15 | 45 | 21 | 18 |
| CMPD 4 | 0.5 | 58 | 10 | 3 | 3 | 0 | 8 | 0 | 16 |
| | 2.0 | 95 | 8 | 0 | 18 | 6 | 11 | 18 | 16 |
| CMPD 5 | 16 | 40 | 6 | 0 | 0 | 0 | 0 | 0 | 10 |
| | 64 | 58 | 0 | 0 | 20 | 0 | 10 | 0 | 10 |
| CMPD 6 | 16 | 25 | 4 | 0 | 8 | 3 | 5 | 0 | 12 |
| | 64 | 66 | 43 | 40 | 48 | 38 | 54 | 45 | 12 |
| CMPD 7 | 1 | 61 | 21 | 16 | 19 | 28 | 31 | 20 | 11 |
| | 4 | 98 | 69 | 55 | 65 | 66 | 60 | 54 | 11 |
| CMPD 8 | 0.5 | 93 | 39 | 26 | 29 | 19 | 21 | 53 | 11 |
| | 2.0 | 98 | 81 | 83 | 85 | 89 | 70 | 84 | 11 |
| CMPD 9 | 250 | 8 | 13 | 0 | 9 | 5 | 9 | 9 | 10 |
| | 1000 | 13 | 13 | 8 | 9 | 15 | 13 | 15 | 10 |
| CMPD 10 | 250 | 16 | 25 | 13 | 19 | 20 | 18 | 18 | 25 |
| | 1000 | 51 | 61 | 46 | 46 | 54 | 51 | 54 | 25 |
| CMPD 11 | 16 | 49 | 39 | 41 | 44 | 41 | 45 | 10 | |
| | 64 | 75 | 73 | 61 | 60 | 61 | 74 | 68 | 10 |

Mean % injury = average injury of two replications rated at two dates.
[a]No data.

Increased Sulfonylurea Resistance and Cross Resistance of W4-4 to Other Classes of AlS Inhibitors at the Whole Plant Level Because W4-4 was confirmed as having a higher level of sulfonylurea resistance than W20 and cross resistance to an imidazolinone at the ALS enzyme level, it was suspected that W4-4 would also demonstrate such resistance at the whole plant level. To investigate this hypothesis, a postemergence herbicide spray test was conducted to compare the reaction of W4-4 to both W20 and wild-type Williams. The applicant was particularly interested in the resistance of W4-4 to herbicide treatments that were injurious to both Williams and W20 in a previous test (Table VII). Herbicide treatments that were significantly injurious (greater than 30% injury) to W20 were selected to test the resistance of W4-4. Hence, applications of Compounds 6, 7, and 8 were selected to test W4-4's reaction to sulfonylureas and applications of Compound 11 were selected to test W4-4's reaction to an imidazolinone. Twenty-four plants each of W4-4, W20, and Williams were planted in separate 10 cm pots and allowed to grow to the second trifoliolate stage. Each pot constituted a single experimental unit receiving a single herbicide treatment. Herbicide treatments (Table VIIA) were applied as described for the first postemergence test and were replicated twice. Control plants were sprayed with the spray carrier solution only (water with 0.25% X77 surfactant). At two weeks after treatment, each plant was rated for % herbicide injury as described in Table VIII. Analysis of variance on injury ratings was performed separately for each herbicide to calculate treatment means and standard errors. Fisher's least significant difference (LSD) was used to determine the significance of line means differences at each herbicide rate using the 95% level of confidence.

TABLE VII-A

Comparison of Mutant W4-4 to Mutant W20 and Williams 82 in terms of Response to Postemergence Application of Four ALS Inhibitor Herbicides

| Herbicide | Rate g/ha | WM82 | W20 mean % injury | W4-4 | LSD (0.05) |
|---|---|---|---|---|---|
| CMPD 6 | 64 | 60 | 10 | 0 | 14.9 |
|  | 125 | 68 | 28 | 8 | 14.9 |
| CMPD 7 | 4 | 83 | 28 | 10 | 6.8 |
|  | 16 | 93 | 43 | 30 | 6.8 |
|  | 32 | 90 | 83 | 43 | 6.8 |
| CMPD 8 | 4 | 90 | 90 | 48 | 4.9 |
|  | 16 | 95 | 93 | 48 | 4.9 |
|  | 32 | 95 | 95 | 65 | 4.9 |
| CMPD 11 | 64 | 73 | 48 | 38 | 7.6 |
|  | 125 | 83 | 80 | 53 | 7.6 |

The preceding test in Table VII-A shows some resistance of W20 and W4-4 soybeans to Compound 11, an imidizaloninone, at higher rates. The field use rate test shown in Table VIIB provides an even more impressive demonstration of the superior resistance to Compound 11 of W20 relative to Williams, and of W4-4 relative to W20.

TABLE VII-B

| Herbicide | Rate g/ha | WM82 | W20 mean % injury | W4-4 |
|---|---|---|---|---|
| CMPD 11 | 8 | 50 | 20 | 0 |
|  | 17.5 | 60 | 30 | 5 |
|  | 35 | 75 | 60 | 25 |

TABLE VIII

Injury Scale for Rating Plants Treated With Post-emergence Applied Sulfonylurea or Imidazolinone Herbicides

| Rating (% injury) | Visual Symptoms |
|---|---|
| 0 | No apparent injury compared to untreated controls. |
| 10 | Slightly stunted. |
| 20 | Noticeable stunting and/or slight reddening of pulvini. |
| 30 | Stunted with reddening, and chlorosis/reddening of apex. |
| 40 | More stunting, reddening, and chlorosis/reddening of apex. |
| 50 | Stunting which reduces plant to ½ of the size of control plants, severe reddening and inhibition of apical bud. |
| 60 | Severe stunting and vein reddening but recovery is probable. |
| 70 | Severe stunting and leaf necrosis evident. Recovery possible but plant will be very weak. |
| 80 | Severe stunting and necrosis of apex, upper leaves, and stem. Recovery doubtful. |
| 90 | Very little growth and most of plant tissue is necrotic. |
| 100 | No shoot growth and/or plant is completely necrotic. |

Test C

Demonstration of Resistance of Preemergence (Soil) Sulfonylurea Application

After demonstration of postemergence sulfonylurea resistance, tests were conducted to determine whether mutant W20 (representative of the new class of dominant mutants) could also resist applications of sulfonylureas applied to soil in which the mutant seeds were planted (preemergence application). The following example is representative of the preemergence sulfonylurea resistance displayed by soybean mutants with dominant sulfonylurea resistance.

W20, a line homozygous for a dominant sulfonylurea-resistance mutation, was compared to Williams 82 in terms of response to preemergence application of three sulfonylurea herbicides. The experimental unit consisted of a single 18 cm pot filled with soil (Sassafras loamy sand with 0.8% organic matter and pH 6.7) in which 6 seeds of a given soybean line were planted 2 cm deep. After planting, each pot was sprayed (using a conveyor belt spray apparatus to emulate field application) with one of 22 different treatments including a check sprayed with AGWT (90% acetone, 4% glycerol, 4% water, 2% Tween-20), and 21 different herbicide treatments using AGWT as a carrier. The herbicide treatments included 7 different concentrations (Table IX) each of three sulfonyl-ureas: Compound 5, Compound 4, and Compound 1. Each herbicide x line treatment was replicated three times. After herbicide treatment, pots were transferred to a greenhouse and arranged in a randomized complete block design. Nineteen days after treatment, each pot was rated visually for herbicide injury using the scale described previously. For each herbicide, analysis of variance on injury ratings was performed separately. Fisher's least significant difference (LSD) was used to determine the significance of line mean differences at each rate using the 95% level of confidence.

Based on responses to increasing preemergence sulfonylurea rates, 10 to 30 times as much herbicide was required to injure W20 as compared to Williams 82 (Table IX). W20 showed agronomically acceptable levels of herbicide injury (less than 30%) to many of the preemergence sulfonylurea treatments that severely injured Williams 82 (Table IX). W20 is clearly resistant to some of the sulfonylurea rates and clearly more tolerant than Williams 82 to all treatments except the highest rate of Compound 4.

Results of all phenotypic characterization tests demonstrate the high degree of preemergence and post-emergence sulfonylurea resistance provided by the applicant's new class of soybean mutants.

TABLE IX

Mean Injury of Williams 82 and W20 Soybean Plants at 19 Days After Preemergence Treatment With Three Sulfonylurea Herbicides

| Herbicide | Rate g/ha | % Injury WM 82 | W20 |
|---|---|---|---|
| Compound 5 | 1 | 0 | 0 |
|  | 3 | 0 | 0 |
|  | 10 | 0 | 0 |
|  | 30 | 15 | 3 |
|  | 100 | 47 | 10 |
|  | 300 | 68 | 15 |
|  | 1000 | 92 | 35 |
|  | LSD* | 10 | 10 |
| Compound 4 | 0.3 | 33 | 0 |
|  | 1 | 55 | 0 |
|  | 3 | 88 | 0 |
|  | 10 | 97 | 17 |
|  | 30 | 98 | 68 |
|  | 100 | 100 | 90 |
|  | 300 | 100 | 95 |
|  | LSD* | 9 | 9 |
| Compound 1 | 0.3 | 30 | 0 |
|  | 1 | 50 | 0 |
|  | 3 | 73 | 3 |
|  | 10 | 95 | 3 |
|  | 30 | 100 | 18 |
|  | 100 | 100 | 63 |
|  | 300 | 100 | 65 |
|  | LSD* | 6 | 6 |

*LSD = Fisher's least significant difference at α = 0.05

Test D

Demonstration of Sulfonylureas Resistance at the ALS Enzyme Level

ALS assays were conducted to determine whether the new class of soybean mutants have sulfonylurea resistance at the ALS enzyme level.

Acetolactate synthase (ALS) was extracted from leaves of soybean plants growing vegetatively. The leaves were homogenized in 4 volumes of buffer containing 100 mM hepes (pH 7.5), 1 mM sodium pyruvate, 0.5 mM magnesium chloride, 0.5 mM thiamine pyrophosphate, 10 mM FAD, 10% glycerol, 5% PVPP, and 0.2% mercaptoethanol. The homogenate was filtered through cheese cloth and centrifuged at 20,000 g for 20 min. ALS was precipitated from the supernatant with ammonium sulfate. The enzyme was collected between 20 and 60% saturation by centrifugation at 20,000 g for 20 min. The pellet was resuspended in buffer containing 100 mM Hepes, 1 mM sodium pyruvate, and 0.5 mM magnesium chloride, and desalted on PD-10 columns (Pharmacia) equilibrated with the same buffer. ALS assays were carried out in a final volume of 0.5 mL at 30° C. The final reaction mixture contained 100 mM Hepes (pH 7.5), 1 mM magnesium chloride, 60 mM sodium pyruvate, 0.4 mM thiaminepyrophosphate, 40 mM FAD, and various concentrations of chlorsulfuron. The assays were initiated with the addition of enzyme (100 mL) and terminated with the addition of 50 mL of 6N sulfuric acid. The acidified reaction mixture was heated to 60° C. for 15 min, after which 0.5 mL of 0.5% (W/V) creatine and 0.5 mL of 5% (W/V) napthol (freshly prepared in 2.5 N sodium hydroxide) were added. The reaction mixtures were heated for an additional 15 min at 60° C., and the absorbance was read at 525 nm. Data are expressed in terms of % control (minus Compound 1) activity and are the average of two replications. Fisher's least significant difference (LSD) value (at the 95% level of confidence) was calculated for each Compound 1 concentration to determine the significance of genotype mean differences.

The ALS activity from the leaves of sulfonylurea-resistant mutant lines was significantly higher than the activity of ALS from Williams 82 at all concentrations of Compound 1 (Table X). These results indicate a Compound 1-resistant form of ALS in the leaves of the resistant mutants. The previously described whole-plant cross resistance tests imply that the mutant soybean ALS is less sensitive to sulfonylureas in general.

TABLE X

Percentage of ALS Activity Remaining at Different Concentration of Chlorsulfuron

| Chlorsulfuron mg/l-1 | WM 82 | W19 | W20 | W23 | W28 | LDS* |
|---|---|---|---|---|---|---|
|  | uninhibited ALS activity (% of control) | | | | | |
| 10 | 41.1 | 60.7 | 50.6 | 55.3 | 54.6 | 3.0 |
| 20 | 26.3 | 54.5 | 35.2 | 46.3 | 46.1 | 7.2 |
| 50 | 15.0 | 48.7 | 31.1 | 38.9 | 42.8 | 7.4 |
| 100 | 11.1 | 45.7 | 20.8 | 37.4 | 36.4 | 5.1 |
| 200 | 8.5 | 40.8 | 19.0 | 34.0 | 34.3 | 3.6 |

*LSD = Least significant difference at 95% confidence level.

What is claimed is:

1. A soybean plant derived from mutation breeding containing at least one dominant mutation capable of being expressed in subsequent generations of said plant and conferring resistance to pre- and post-emergent application of a herbicidal compound having the Formula I

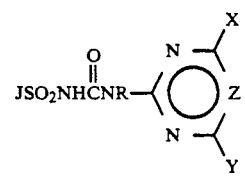

wherein
R is H or CH$_3$;
J is

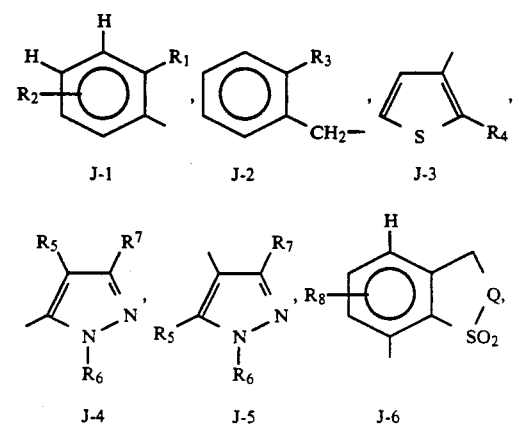

-continued

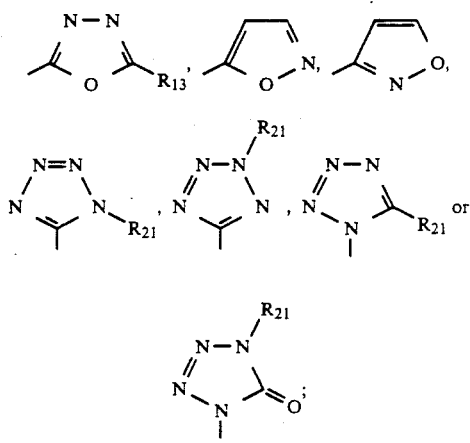

R' is Cl, Br, NO$_2$, C$_1$-C$_4$ alkyl, C$_2$-C$_4$ alkyl, C$_2$-C$_4$ alkenyl, CF$_3$, C$_1$-C$_4$ alkoxy, C$_1$-C$_4$ haloalkoxy, C$_3$-C$_4$ alkenyloxy, C$_2$-C$_4$ haloalkenyloxy, C$_3$-C$_4$ alkynyloxy, CO$_2$R$_9$, CONR$_{10}$R$_{11}$, S(O)mR$_{12}$, OSO$_2$R$_{12}$, phenyl, SO$_2$N(OCH$_3$)CH$_3$, SO$_2$NR$_{10}$R$_{11}$, R$_2$ is H, Cl, Br, F, CH$_3$, NO$_2$, SCH$_3$, OCF$_2$H, OCH$_2$CF$_3$ or OCH$_3$;
R$_3$ is Cl, NO$_2$, CO$_2$CH$_3$, CO$_2$C$_2$H$_5$, SO$_2$N(CH$_3$)$_2$, SO$_2$CH$_3$ or SO$_2$C$_2$H$_5$;
R$_4$ is C$_1$-C$_3$ alkyl, Cl, Br, NO$_2$, CO$_2$R$_9$, CON(CH$_3$)$_2$, SO$_2$N(CH$_3$)$_2$, SO$_2$N(OCH$_3$)CH$_3$ or S(O)$_m$R$_{12}$;
R$_5$ is C$_1$-C$_3$ alkyl, C$_4$-C$_5$ cycloalkylcarbonyl, F, Cl, Br, NO$_2$, CO$_2$R$_{14}$, SO$_2$N(CH$_3$l)$_2$, SO$_2$R$_{12}$ or phenyl;
R$_6$ is H, C$_1$-C$_3$ alkyl, or CH$_2$CH=CH$_2$;
R$_7$ is H, CH$_3$, OCH$_3$, Cl or Br;
R$_8$ is H, F, Cl, Br, CH$_3$, OCH$_3$, CF$_3$, SCH$_3$ or OCF$_2$H;
R$_9$ is C$_1$-C$_4$ alkyl, C$_3$-C$_4$ alkenyl or CH$_2$—CH$_2$Cl;
R$_{10}$ is H or C$_1$-C$_3$ alkyl;
R$_{11}$ is H or C$_1$-C$_2$ alkyl;
R$_{12}$ is C$_1$-C$_3$ alkyl;
R$_{13}$ is H or CH$_3$;
R$_{14}$ is C$_1$-C$_3$ alkyl or CH$_2$CH=CH$_2$;
m is 0, 1 or 2;
n is 1 or 2;
Q is CH$_2$, CHCH$_3$ or NR$_{15}$;
R$_{15}$ is H or C$_1$-C$_4$ alkyl;
R$_{16}$ is H or CH$_3$;
R$_{17}$ is C(O)NR$_{18}$R$_{19}$, CF$_3$, COOCH$_3$ or SO$_2$CH$_2$CH$_3$;
R$_{18}$ is H or CH$_3$;

R$_{19}$ is CH$_3$;
R$_{20}$ is H, Cl, F, Br, CH$_3$, CF$_3$, OCH$_3$ or OCF$_2$H;
R$_{21}$ is H or CH$_3$;
X is CH$_3$, OCH$_3$, OC$_2$H$_5$ or NHCH$_3$;
Y is CH$_3$, C$_2$H$_5$, OCH$_3$, OC$_2$H$_5$, OCF$_2$H, OCH$_2$CF$_3$, Cl, CH$_2$OCH$_3$ or cyclopropyl;
Z is CH or N;
and their agriculturally suitable salts; provided that
a) when Y is Cl, then Z is CH and X is OCH$_3$;
b) when Y is OCF$_2$H, then Z is CH;
c) when J is J-1 and R$_1$ is OSO$_2$R$_{12}$ or phenyl, then Y is other than OCF$_2$H;
d) when JH is J-2, Y is other than OCF$_2$H or OCH$_2$CF$_3$; and
e) when J is J-3 and R$_4$ is S(O)$_m$R$_{12}$, then Y is other than OCH$_2$CF$_3$ said soybean plant being capable of normal trifoliolate development when germinated in and irrigated continuously with a chlorsulfuron solution having a concentration sufficient to prevent normal trifoliolate development of Williams 82 wild type soybean cultivar.

2. A soybean plant of claim 1 wherein said plant is selected by mutation breeding.

3. A soybean plant of claim 2 wherein
J is J-1;
R$_1$ is Cl, CH$_3$, C$_1$-C$_4$ alkoxy, C$_1$-C$_2$ haloalkoxy, allyloxy, propargyloxy, CO$_2$R$_9$, CONR$_{10}$R$_{11}$, SO$_2$N(OCH$_3$)CH$_3$, SO$_2$NR$_{10}$R$_{11}$, S(O)mR$_{12}$, OSO$_2$R$_{12}$, phenyl or

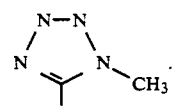

4. A soybean plant of claim 2 wherein
J is J-2;
R is H; and
R$_3$ is SO$_2$N(CH$_3$)$_2$, CO$_2$CH$_3$ or CO$_2$C$_2$H$_5$.
5. A soybean plant of claim 2 wherein
J is J-3
R is H; and
R$_4$ is CO$_2$CH$_3$ or CO$_2$C$_2$H$_5$.
6. A soybean plant of claim 2 wherein
J is J-4;
R is H;
R$_5$ is Cl, Br, CO$_2$CH$_3$, CO$_2$C$_2$H$_5$ or

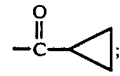

R$_6$ is CH$_3$; and
R$_7$ is H, Cl or OCH$_3$.
7. A soybean plant of claim 2 wherein
J is J-5;
R is H;
R$_5$ is CO$_2$CH$_3$ or CO$_2$C$_2$H$_5$; and
R$_7$ is H or CH$_3$.
8. A soybean plant of claim 2 wherein
J is J-6;
Q is CHCH$_3$ or NR$_{15}$;
R is H; and
R$_8$ is H, F, Cl, CH$_3$, OCH$_3$, CF$_3$ or SCH$_3$.
9. A soybean plant of claim 2 wherein
J is J-7;
R is H; and $R_8$ is H, F, Cl, $CH_3$, $OCH_3$, $CF_3$ or $SCH_3$.

10. A soybean plant of claim 2 wherein
J is J-8;
R is H;
$R_{16}$ is $CH_3$; and
$R_8$ is H, F, Cl, $CH_3$, $OCH_3$, $CF_3$ or $SCH_3$.

11. A soybean plant of claim 2 wherein
J is J-9; and
R is H; and
$R_{17}$ is $C(O)N(CH_3)_2$, $CF_3$, $COOCH_3$ or $SO_2CH_2CH_3$.

12. A soybean plant of claim 2 wherein
R is H;
$R_1$ is Cl, $C_1$-$C_4$ alkoxy, $OCF_2H$, $OCH_2CH_2Cl$, $CO_2R_9$, $CON(CH_3)_2$, $SO_2N(CH_3)_2$, $SO_2R_{12}$ or $OSO_2R_{12}$; and
$R_2$ is H, Cl, $CH_3$, or $OCH_3$.

13. A soybean plant of claim 2 wherein said herbicidal compound is selected from the group consisting of:
2-chloro-N-[(4-methoxy-6-methyl-1,3,5-triazin-2-yl)aminocarbonyl]benzenesulfonamide,
methyl 2-[[[[(4,6-dimethyl-2-pyrimidinyl)amino]carbonyl]amino]sulfonyl]benzoate,
methyl 2-[[[[(4-methoxy-6-methyl-1,3,5-triazin-2-yl)amino]carbonyl]sulfonyl]benzoate,
2-[[N-(4-methoxy-6-methyl-1,3,5-triazin-2-yl)-N-methylaminocarbonyl]aminosulfonyl]benzoic acid, methyl ester,
ethyl 2-[[[[(4-chloro-6-methoxy-2-pyrimidinyl)amino]carbonyl]amino]sulfonyl]benzoate,
2-[[(4-ethoxy-6-methylamino-1,3,5-triazin-2-yl)aminocarbonyl]aminosulfonyl]benzoic acid, methyl ester,
2-[[(4,6-dimethoxy-1,3,5-triazin-2-yl)aminocarbonyl]aminosulfonyl]-4-(2,2,2-trifluoroethoxy)benzoic acid, ethyl ester,
4-chloro-2-[[(4-methoxy-6-methyl-1,3,5-triazin-2-yl)aminocarbonyl]aminosulfonyl]benzoic acid, isopropyl ester,
3-[[[[(4-methoxy-6-methyl-1,3,5-triazin-2-yl)amino]carbonyl]amino]sulfonyl]-2-thiophene carboxylic acid, methyl ester,
methyl 2-[[[[(4-6-dimethoxy-2-pyrimidinyl)amino]carbonyl]amino]sulfonyl]methylbenzoate,
2-[[(4,6-dimethoxypyrimidin-2-yl)aminocarbonyl]aminosulfonyl]-N,N-dimethyl-3-pyridinecarboxamide,
2-[[(4,6-dimethoxypyrimidin-2-yl)aminocarbonyl]aminosulfonyl]-3-pyridinecarboxylic acid, methyl ester,
N-[(4,6-dimethoxypyrimidin-2-yl)aminocarbonyl]-3-(ethylsulfonyl)-2-pyridinesulfonamide,
N-[4,6-dimethoxypyrimidin-2-yl)aminocarbonyl]-2,3-dihydro-2-methyl-benzo(b)thiophene-7-sulfonamide, 1,1 dioxide,
2[[[[(4,6-bis(difluoromethoxy)-2-pyrimidinyl]amino]carbonyl]amino]sulfonyl]benzoic acid, methyl ester,
ethyl 5-[3-(4,6-dimethoxypyrimidin-2-yl)ureidosulfonyl]-1-methylpyrazole-4-carboxylate,
N-[(6-methoxy-4-methyl-1,3,5-triazin-2-yl)aminocarbonyl]-2-(2-chloroethoxy)benzene sulfonamide, and
N-[(4,6-dimethoxy-1,3,5-triazin-2-yl)aminocarbonyl]-3-trifluoromethyl-2-pyridinesulfonamide.

14. A soybean plant of claim 13 wherein said herbicidal compound is:
methyl 2-[[[[(4,6-dimethyl-2-pyrimidinyl)-amino]carbonyl]sulfonyl]benzoate.

15. A soybean plant derived from mutation breeding containing at least one dominant mutation capable of being expressed in subsequent generations of said plant and conferring resistance to pre- and postemergent application of an herbicidal compound having the Formula II:

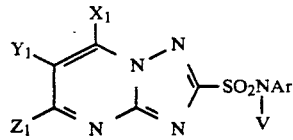

wherein
Ar is

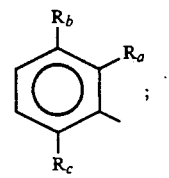

$R_a$ is $C_1$-$C_4$ alkyl, F, Cl, Br, I, $NO_2$, $S(O)_pR_d$, $COOR_e$ or $CF_3$;
$R_b$ is H, F, Cl, Br, I, $C_1$-$C_4$ alkyl, $CF_2$ or $COOR_e$;
$R_c$ is H, $C_1$-$C_4$ alkyl, F, Cl, Br, I, $CH_2OR_d$, $CF_2$, phenyl, $NO_2$ or $COOR_e$;
$R_d$ is $C_1$-$C_4$ alkyl;
$R_e$ is $C_1$-$C_4$ alkyl, $C_1$-$C_4$ alkenyl, $C_1$-$C_4$ alkynyl, or 2-ethoxyethyl;
V is H, $C_1$-$C_3$ alkyl, allyl, propargyl, benzyl or $C_1$-$C_3$ alkylcarbonyl;
$X_1$, $Y_1$, and $Z_1$, are independently H, F, Cl, Br, I, $C_1$-$C_4$ alkyl $C_1$-$C_2$ alkylthio or $C_1$-$C_4$ alkoxy; and
p of 0, 1 or 2
said soybean plant being capable of normal trifoliolate development when germinated in and irrigated continuously with a chlorsulfuron solution having a concentration sufficient to prevent normal trifoliolate development of Williams 82 wild type soybean cultivar.

16. A soybean plant of claim 15 wherein said plant is selected by mutation breeding.

17. A soybean plant of claim 16 wherein V is H.

18. A soybean plant of claim 16 wherein $X_1$ is H or $CH_3$ $Y_1$ is H; $Z_1$ is $CH_3$; and $R_a$ and $R_c$ are not simultaneously H.

19. A soybean plant derived from mutation breeding containing at least one dominant mutation capable of being expressed in subsequent generations of said plant and conferring resistance to pre- and postemergent application of a herbicidal compound having the Formula III:

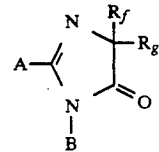

wherein
A is

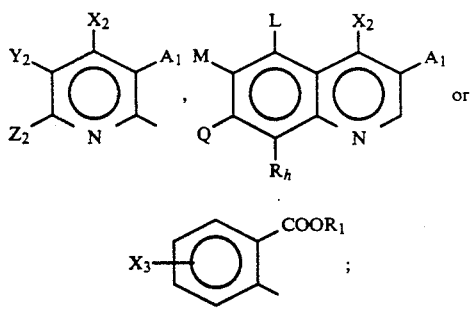

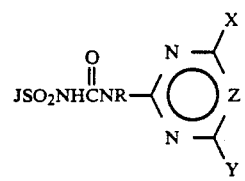

- $R_f$ is $C_1$–$C_4$ alkyl;
- $R_g$ is $C_1$–$C_4$ alkyl or $C_3$–$C_6$ cycloalkyl;
- $A_1$ is $COOR_i$, $CH_2OH$ or $CHO$;
- $R_i$ is H; $C_1$–$C_{12}$ alkyl optionally substituted by $C_1$–$C_3$ alkyl, $C_3$–$C_6$ cycloalkyl or phenyl; $C_3$–$C_5$ alkenyl optionally substituted by phenyl or 1–2 $C_1$–$C_3$ alkyl, F, Cl, Br or I; or $C_3$–$C_5$ alkynyl optionally substituted by phenyl or 1–2 $C_1$–$C_3$ alkyl, F, Cl, Br or I;
- B is H, $C(O)C_1$–$C_6$ alkyl or $C(O)$phenyl optionally substituted by Cl, $NO_2$ or $OCH_3$;
- $X_2$ is H, F, Cl, Br, I, OH or $CH_3$;
- $Y_2$ and $Z_2$ are independently H, $C_1$–$C_6$ alkyl, $C_1$–$C_6$ alkoxy, F, Cl, Br, I, phenyl, $NO_2$, CN, $CF_3$ or $SO_2CH_3$; or
- $Y_2$ and $Z_2$ together with the carbon atoms to which they are attached form a 5- or 6-membered saturated or unsaturated ring containing 1–3 heteroatoms selected from the group consisting of 0–2 oxygen, 0–2 sulfur and 0–3 nitrogen atoms; said ring may be unsubstituted or substituted on carbon or nitrogen wherein the substituents are selected from the group consisting of $C_1$–$C_4$ alkyl, $C_1$–$C_4$ haloalkyl, $C_3$–$C_6$ alkenyl, $C_3$–$C_6$ haloalkenyl, $C_3$–$C_4$ alkynyl, $C_3$–$C_4$ haloalkynyl, $C_1$–$C_4$ alkoxy, $C_1$–$C_4$ haloalkoxy, $C_1$–$C_4$ alkoxycarbonyl, phenyl, $C_1$–$C_4$ dialkylamino and $C_1$–$C_4$ alkylsulfonyl;
- $X_3$ is H, $CH_3$, Cl or $NO_2$;
- L is M, Q and $R_h$ are independently H, F, Cl, Br, I, $CH_3$, $OCH_3$, $NO_2$, $CF_3$, CN, $N(CH_3)_2$, $NH_2$, $SCH_3$ or $SO_2CH_3$ provided that only one of M or Q may be a substituent other than H,
- F, Cl, Br, I, $CH_3$ or $OCH_3$ said soybean plant being capable of normal trifoliolate development when germinated in and irrigated continuously with a chlorsulfuron solution having a concentration sufficient to prevent normal trifoliolate development of Williams 82 wild type soybean cultivar.

20. A soybean plant of claim 19 wherein said plant is selected by mutation breeding.

21. A soybean plant of claim 20 wherein:
- B is H; and
- $A_1$ is $COOR_i$.

22. A soybean plant of claim 20 wherein:
- $R_f$ is $CH_3$;
- $R_g$ is $CH(CH_3)_2$;
- $X_2$ is H;
- $Y_2$ is H or $C_1$–$C_3$ alkyl or $OCH_3$;
- $Z_2$ is H;
- $X_3$ is H, $CH_3$, Cl or $NO_2$; and
- L, M, Q and $R_h$ are H.

23. Seed obtained by growing a soybean plant of claims 1–21 or 22.

24. A method for controlling the growth of undesired vegetation growing at a locus where a soybean plant of any one of claims 1–14 has been cultivated comprising applying to the locus an effective amount of herbicidal compound of Formula I

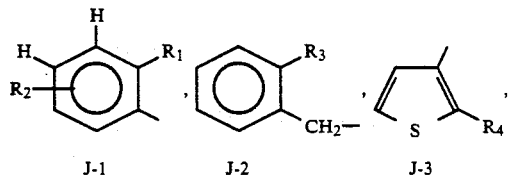

wherein
R is H or $CH_3$;
J is

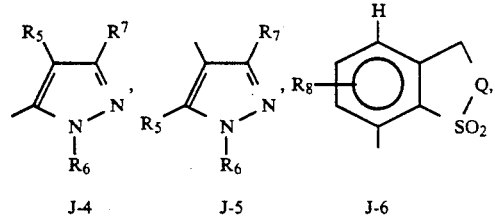

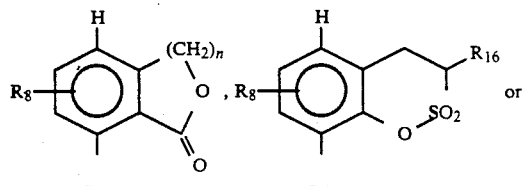

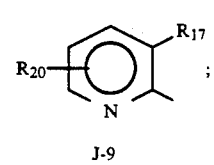

$R_1$ is Cl, Br, $NO_2$, $C_1$–$C_4$ alkyl, $C_2$–$C_4$ alkenyl, $CF_3$, $C_1$–$C_4$ alkoxy, $C_1$–$C_4$ haloalkoxy, $C_3$–$C_4$ alkenyloxy, $C_2$–$C_4$ haloalkenyloxy, $C_3$–$C_4$ alkynyloxy, $CO_2R_9$, $CONR_{10}R_{11}$, $S(O)mR_{12}$, $OSO_2R_{12}$, phenyl, $SO_2N(OCH_3)CH_3$, $SO_2NR_{10}R_{11}$,

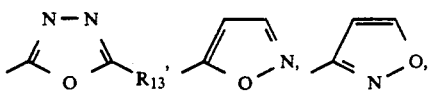

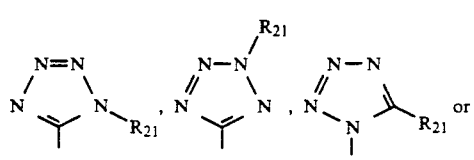

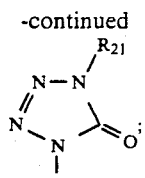

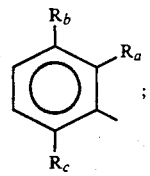

$R_2$ is H, Cl, Br, F, CH$_3$, NO$_2$, SCH$_3$, OCF$_2$H, OCH$_2$CF$_3$ or OCH$_3$;

$R_3$ is Cl, NO$_2$, CO$_2$CH$_3$, CO$_2$C$_2$H$_5$, SO$_2$N(CH$_3$)$_2$, SO$_2$CH$_3$ or SO$_2$C$_2$H$_5$;

$R_4$ is C$_1$-C$_3$ alkyl, Cl, Br, NO$_2$, CO$_2$R$_9$, CON(CH$_3$)$_2$, SO$_2$N(CH$_3$)$_2$, SO$_2$N(OCH$_3$l)CH$_3$ or S(O)$_m$R$_{12}$;

$R_5$ is C$_1$-C$_3$ alkyl, C$_4$-C$_5$ cycloalkylcarbonyl, F, Cl, Br, NO$_2$, CO$_2$R$_{14}$, SO$_2$N(CH$_3$)$_2$, SO$_2$R$_{12}$ or phenyl;

$R_6$ is H, C$_1$-C$_3$ alkyl, or CH$_2$CH=CH$_2$;

$R_7$ is H, CH$_3$, OCH$_3$, Cl or Br;

$R_8$ is H, F, Cl, Br, CH$_3$, OCH$_3$, CF$_3$, SCH$_3$ or OCF$_2$H;

$R_9$ is C$_1$-C$_4$ alkyl, C$_3$-C$_4$ alkenyl or CH$_2$—CH$_2$Cl;

$R_{10}$ is H or C$_1$—C$_3$ alkyl;

$R_{11}$ is H or C$_1$-C$_2$ alkyl;

$R_{12}$ is C$_1$-C$_3$ alkyl;

$R_{13}$ is H or CH$_3$;

$R_{14}$ is C$_1$-C$_3$ alkyl or CH$_2$CH=CH$_2$;

m is 0, 1 or 2;

n is 1 or 2.

Q is CH$_2$, CHCH$_3$ or NR$_{15}$;

$R_{15}$ is H or C$_1$-C$_4$ alkyl;

$R_{16}$ is H or CH$_3$;

$R_{17}$ is C(O)NR$_{18}$R$_{19}$, CF$_3$, COOCH$_3$ or SO$_2$CH$_2$CH$_3$;

$R_{18}$ is H or CH$_3$;

$R_{19}$ is CH$_3$;

$R_{20}$ is H, Cl, F, Br, CH$_3$, CF$_3$, OCH$_3$ or OCF$_2$H;

$R_{21}$ is H or CH$_3$;

X is CH$_3$, OCH$_3$, OC$_2$H$_5$ or NHCH$_3$;

Y is CH$_3$, C$_2$H$_5$, OCH$_3$, OC$_2$H$_5$, OCF$_2$H, OCH$_2$CF$_3$, Cl, CH$_2$OCH$_3$ or cyclopropyl;

Z is CH or N;

and their agriculturally suitable salts;

provided that
a) when Y is Cl, then Z is CH and X is OCH$_3$;
b) when Y is OCF$_2$H, then Z is CH;
c) when J is J-1 and R$_1$ is OSO$_2$R$_{12}$ or phenyl, then Y is other than OCF$_2$H;
d) when J is J-2, then Y is other than OCF$_2$H or OCH$_2$CF$_3$; and
e) when J is J-3 and R$_4$ is S(O)$_m$R$_{12}$, then Y is other than OCH$_2$CF$_3$.

25. A method for controlling the growth of undesired vegetation growing at a locus where a soybean plant of any one of claims 15, 16, 17 or 18 has been cultivated comprising applying to the locus an effective amount of herbicidal compound of Formula II

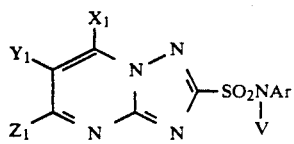

wherein
Ar is $R_a$ is C$_1$-C$_4$ alkyl, F, Cl, Br, I, NO$_2$, S(O)$_p$R$_d$, COOR$_e$ or CF$_3$;

$R_b$ is H, F, Cl, Br, I, C$_1$-C$_4$ alkyl, CF$_2$ or COOR$_e$;

$R_c$ is H, C$_1$-C$_4$ alkyl, F, Cl, Br, I, CH$_2$OR$_d$, CF$_2$, phenyl, NO$_2$ or COOR$_e$;

$R_d$ is C$_1$-C$_4$ alkyl;

$R_e$ is C$_1$-C$_4$ alkyl, C$_1$-C$_4$ alkenyl, C$_1$-C$_4$ alkynyl, or 2-ethoxyethyl;

V is H, C$_1$-C$_3$ alkyl, allyl, propargyl, benzyl or C$_1$-C$_3$ alkylcarbonyl;

$X_1$, $Y_1$, and $Z_1$, are independently H, F, Cl, Br, I, C$_1$-C$_4$ alkyl C$_1$-C$_2$ alkylthio or C$_1$-C$_4$ alkoxy; and p is 0, 1 or 2.

26. A method for controlling the growth of undesired vegetation growing at a locus where a soybean plant of any one of claims 19, 20, 21 or 22 has been cultivated comprising applying to the locus an effective amount of herbicidal compound of Formula III

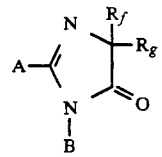

wherein
A is

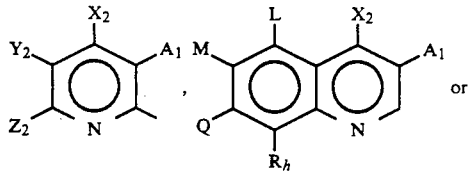

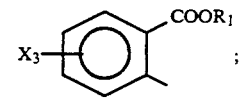

$R_f$ is C$_1$-C$_4$ alkyl;

$R_g$ is C$_1$-C$_4$ alkyl or C$_3$-C$_6$ cycloalkyl;

$A_1$ is COOR$_i$, CH$_2$OH or CHO;

$R_i$ is H; C$_1$-C$_{12}$ alkyl optionally substituted by C$_1$-C$_3$ alkyl, C$_3$-C$_6$ cycloalkyl or phenyl; C$_3$-C$_5$ alkenyl optionally substituted by phenyl or 1-2 C$_1$-C$_3$ alkyl, F, Cl, Br or I; or C$_3$-C$_5$ alkynyl optionally substituted by phenyl or 1-2 C$_1$-C$_3$ alkyl, F, Cl, Br or I;

B is H; C(O)C$_1$-C$_6$ alkyl or C(O)phenyl optionally substituted by Cl, NO$_2$ or OCH$_3$;

$X_2$ is H, F, Cl, Br, I, OH or CH$_3$;

$Y_2$ and $Z_2$ are independently H, C$_1$-C$_6$ alkyl, C$_1$-C$_6$ alkoxy, F, Cl, Br, I, phenyl, NO$_2$, CN, CF$_3$ or SO$_2$CH$_3$; or $Y_2$ and $Z_2$ together with the carbon atoms to which they are attached form a 5- or 6-membered saturated or unsaturated ring containing 1-3 heteroatoms selected from the group consisting of 0-2 oxygen, 0-2 sulfur and 0-3 nitrogen atoms; said ring may be unsubstituted or substituted on carbon or nitrogen wherein the substituents are selected from the group consisting of $C_1$-$C_4$ alkyl, $C_1$-$C_4$ haloalkyl, $C_3$-$C_6$ alkenyl, $C_3$-$C_6$ haloalkenyl, $C_3$-$C_4$ alkynyl, $C_3$-$C_4$ haloalkynyl, $C_1$-$C_4$ alkoxy, $C_1$-$C_4$ haloalkoxy, C1-C4 alkoxycarbonyl, phenyl, $C_1$-$C_4$ dialkylamino and $C_1$-$C_4$ alkylsulfonyl;

L is M, Q and $R_h$ are independently H, F, Cl, Br, I, $CH_3$, $OCH_3$, $HNO_2$, $CF_3$, CN, $N(CH_3)_2$, $NH_2$, $SCH_3$ or $SO_2CH_3$ provided that only one of M or Q may be a substituent other than H, F, Cl, Br, I, $CH_3$ or $OCH_3$.

* * * * *